US007151958B2

(12) United States Patent
Hsu et al.

(10) Patent No.: US 7,151,958 B2
(45) Date of Patent: *Dec. 19, 2006

(54) SYSTEM AND METHOD OF CLASSIFYING TACHYARRHYTHMIA EPISODES AS ASSOCIATED OR DISASSOCIATED

(75) Inventors: William Hsu, Circle Pines, MN (US); Robert J. Sweeney, Woodbury, MN (US); Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 785 days.

This patent is subject to a terminal disclaimer.

(21) Appl. No.: 10/211,222

(22) Filed: Aug. 2, 2002

(65) Prior Publication Data

US 2002/0198461 A1  Dec. 26, 2002

Related U.S. Application Data

(63) Continuation of application No. 09/452,670, filed on Dec. 1, 1999, now Pat. No. 6,456,871.

(51) Int. Cl.
*A61B 5/046* (2006.01)
(52) U.S. Cl. ...................... 600/518; 600/515
(58) Field of Classification Search ............... 600/515, 600/518, 519, 521; 607/14, 9
See application file for complete search history.

(56) References Cited

U.S. PATENT DOCUMENTS

| 4,583,553 | A | 4/1986 | Shah et al. ............... 128/704 |
| 5,002,052 | A | 3/1991 | Haluska ................ 128/419 PG |
| 5,183,040 | A | 2/1993 | Nappholz et al. ...... 128/419 PG |
| 5,184,615 | A | 2/1993 | Nappholz et al. ...... 128/419 PG |
| 5,193,535 | A | 3/1993 | Bardy et al. ............. 128/419 D |
| 5,193,550 | A * | 3/1993 | Duffin ........................ 600/510 |
| 5,203,326 | A | 4/1993 | Collins ................. 128/419 PG |
| 5,205,283 | A * | 4/1993 | Olson ............................ 607/4 |
| 5,217,021 | A | 6/1993 | Steinhaus et al. ........... 128/702 |
| 5,251,621 | A | 10/1993 | Collins ........................... 607/4 |
| 5,257,621 | A | 11/1993 | Bardy et al. ................... 607/5 |
| 5,311,874 | A | 5/1994 | Baumann et al. ........... 128/705 |
| 5,327,900 | A | 7/1994 | Mason et al. |

(Continued)

FOREIGN PATENT DOCUMENTS

EP    0617980    10/1994

OTHER PUBLICATIONS

LeCarpentier, G L., "Differentiation of sinus tachycardia from ventricular tachycardia with 1:1 ventriculoatrial conduction in dual chamber implantable cardioverter defibrillators: feasibility of a criterion based on the atrioventricular interval", *Pacing Clin Electrophysiol.*, 17(11 Pt 1), (Nov. 1994), 1818-31.

(Continued)

*Primary Examiner*—Kennedy Schaetzle
(74) *Attorney, Agent, or Firm*—Schwegman, Lundberg, Woessner & Kluth, P.A.

(57) ABSTRACT

A method and system for classifying tachyarrhythmia episodes as associated or disassociated. Primary and auxiliary depolarizations are detected from different cardiac regions during a tachycardia episode. A first time interval is positioned to surround each of one or more primary depolarizations, including auxiliary depolarizations that occur in the first time interval. The auxiliary depolarizations occurring in the first time interval are then counted. Based on the number and the location of the auxiliary depolarizations counted in the first time intervals, the one or more primary depolarizations and the auxiliary depolarizations of the tachycardia episode are classified as disassociated or associated.

49 Claims, 8 Drawing Sheets

U.S. PATENT DOCUMENTS

| | | | |
|---|---|---|---|
| 5,379,776 A | | 1/1995 | Murphy et al. ............. 128/705 |
| 5,383,910 A | * | 1/1995 | den Dulk .................... 607/14 |
| 5,713,932 A | | 2/1998 | Gillberg et al. |
| 5,730,141 A | | 3/1998 | Fain et al. .................. 128/705 |
| 5,776,072 A | | 7/1998 | Hsu et al. ................... 600/518 |
| 5,836,975 A | | 11/1998 | DeGroot ........................ 607/5 |
| 5,836,976 A | | 11/1998 | Min et al. ...................... 607/6 |
| 5,868,793 A | | 2/1999 | Nitzsche et al. ............... 607/5 |
| 5,873,897 A | | 2/1999 | Armstrong et al. ........... 607/14 |
| 5,882,352 A | | 3/1999 | Duncan et al. ................. 607/4 |
| 5,891,043 A | | 4/1999 | Ericksen et al. ............ 600/508 |
| 5,891,170 A | | 4/1999 | Nitzsche et al. ............... 607/4 |
| 5,893,882 A | | 4/1999 | Peterson et al. .............. 607/14 |
| 5,954,752 A | | 9/1999 | Mongeon et al. ............... 607/6 |
| 5,968,079 A | | 10/1999 | Warman et al. ................ 607/5 |
| 5,978,700 A | | 11/1999 | Nigam ....................... 600/518 |
| 5,978,707 A | | 11/1999 | Krig et al. .................... 607/14 |
| 5,987,356 A | | 11/1999 | DeGroot ........................ 607/5 |
| 6,007,493 A | | 12/1999 | Ericksen et al. ............ 600/508 |
| 6,456,871 B1 | * | 9/2002 | Hsu et al. ................... 600/518 |
| 2005/0021097 A1 | | 1/2005 | Thompson et al. |

OTHER PUBLICATIONS

Nair, M , "Automatic arrhythmia identification using analysis of the atrioventricular association. Application to a new generation of implantable defibrillators. Participating Centers of the Automatic Recognition of Arrhythmia Study Group.", *Circulation*, 95(4), (Feb. 1997),967-73.

Stevenson, S A., "A:V = 1:1 cardiac arrhythmia detection by VA interval analysis", *J Electrocardiol.*, 29 Suppl, (1996),198-201.

Thompson, Julie A., "An Improved Method of Discriminationof 1:1 Tachycardias using a Variance Based Model of Electrical Conduction of the Heart", *Ph. D. Dissertation, University of Michigan*, (2000), 194 pgs.

Thompson, Julie , "Improved Differentiation of 1:1 Tachycardias in Dual-Chamber ICDs Using Interval Variability", *Noth American Society of Pacing and Electrophysiology (NASPE) Conference held in Boston, MA on May 4, 2001.*, 14.

Thompson, J , "Recognition of ventricular tachycardia with 1:1 retrograde atrial activation: A new algorithm for implantable cardioverter defibrillators", *Proceedings of the 19th Annual International Conference of the IEEE Engineering in Medicine and Biology Society. 'Magnificent Milestones and Emerging Opportunities in Medical Engineering'*, pt. 1, vol. 1 (1997),393-4.

Thompson, J A., "Ventriculoatrial conduction metrics for classification of ventricular tachycardia with 1:1 retrograde conduction in dual-chamber sensing implantable cardioverter defibrillators", *J Electrocardiol.*, 31 Suppl, (1998),152-6.

Throne, R D., "Discrimination of retrograde from anterograde atrial activation using intracardiac electrogram waveform analysis", *Pacing Clin Electrophysiol.*, 12(10), (Oct. 1989), 1622-30.

* cited by examiner

SYSTEM AND METHOD OF CLASSIFYING TACHYARRHYTHMIA EPISODES AS ASSOCIATED OR DISASSOCIATED

CROSS-REFERENCE TO RELATED APPLICATION(S)

This patent application is a continuation of U.S. patent application Ser. No. 09/452,670, now U.S. Pat. No. 6,456,871 filed on Dec. 1, 1999, the specification of which is hereby incorporated by reference.

FIELD OF THE INVENTION

This invention relates generally to the field of medical devices, and more particularly to an implantable medical device for analyzing and classifying tachycardia episodes.

BACKGROUND

The heart is generally divided into four chambers, two atrial chambers and the two ventricular chambers. As the heart beats, the atrial chambers and the ventricular chambers of the heart go through a cardiac cycle. The cardiac cycle consists of one complete sequence of contraction and relaxation of the chambers of the heart. The terms systole and diastole are used to describe the contraction and relaxation phases the chambers of the heart experience during a cardiac cycle. In systole, the ventricular muscle cells are contracting to pump blood through the circulatory system. During diastole, the ventricular muscle cells relax, causing blood from the atrial chambers to fill the ventricular chambers. After the period of diastolic filling, the systolic phase of a new cardiac cycle is initiated.

Control over the timing and order of the atrial and ventricular contractions during the cardiac cycle is critical for the heart to pump blood efficiently. Efficient pumping action of the heart requires precise coordination of the contraction of individual cardiac muscle cells. Contraction of each cell is triggered when an electrical excitatory impulse (an "action potential") sweeps over the heart. Proper coordination of the contractual activity of the individual cardiac muscle cells is achieved primarily by the conduction of the action potential from one cell to the next by gap junctions that connect all cells of the heart into a functional system. In addition, muscle cells in certain areas of the heart are specifically adapted to control the frequency of cardiac excitation, the pathway of conduction and the rate of impulse propagation through various regions of the heart. The major components of this specialized excitation and conduction system include the sinoatrial node (SA node), the atrioventricular node (AV node), the bundle of His, and specialized cells called Purkinje fibers.

The SA node is located at the junction of the superior vena cava and the right atrium. Specialized atrium muscle cells of the SA node spontaneously generate action potentials which are then propagated through the rest of the heart to cause cardiac contraction. This SA node region normally acts as the intrinsic cardiac pacemaker. The action potential generated by the SA node spreads through the atrial wall, causing the atrial chambers to contract and the P-wave of an electrocardiogram signal.

The AV node consists of small, specialized cells located in the lower portion of the atrial chamber. The AV node acts like a bridge for the action potential to cross over into the ventricular chamber of the heart. Once the action potential has crossed over to the ventricular chambers, the bundle of His carries the action potential to specialized cardiac fibers called Purkinje fibers. The Purkinje fibers then distribute the action potential throughout the ventricular chamber of the heart. This results in rapid, very nearly simultaneous excitation of all ventricular muscle cells. The conduction of the action potential through the AV node and into the ventricular chambers creates the QRS-complex of an electrogram signal.

During the cardiac cycle, the action potential moves in an antegrade direction, first causing the atrial chambers to contract and then causing the ventricle chambers to contract. When this occurs the depolarization of the atria is "associated" with the depolarization of the ventricle. However, there are cardiac conditions in which the depolarizations (i.e., contractions) occurring in one chamber of the heart are not associated with subsequent contractions occurring in another chamber of the heart. In these situations, the contractions of these regions of the heart are "disassociated."

The ability to identify and classify the cardiac depolarizations occurring during a cardiac episode, such as a tachycardia episode, as either associated and disassociated is important for directing any additional analysis of the cardiac episode and for directing the appropriate therapy to treat the cardiac episode. One situation where classifying atrial and ventricular contractions of a tachycardia episode as being either associated or disassociated is in the discrimination, or classification, of ventricular tachycardia episodes from supraventricular tachycardia episodes. The ability to accurately classify a ventricular tachycardia episode from a supraventricular tachycardia episode allows the mechanism of the tachycardia episode to be identified which helps greatly in directing appropriate therapy. A need, however, still exists for a reliable way of classifying the cardiac depolarizations occurring during cardiac episodes as either associated or disassociated.

SUMMARY OF THE INVENTION

The present subject matter allows for cardiac depolarizations sensed during a cardiac episode in different cardiac regions to be classified as either being associated or disassociated. In one embodiment, the present subject matter relies upon isolating cardiac depolarizations sensed during a tachycardia episode in windows. The cardiac depolarizations within the windows are then counted, and based on the number and the location of the cardiac depolarizations within the windows the association or the disassociation of the cardiac depolarizations occurring during the cardiac episode can be determined. The present subject matter, thus, provides for accurate classification of cardiac episodes as either associated or disassociated which allows the mechanism of the tachycardia episode to be identified and which helps greatly in directing appropriate therapy to treat the cardiac episode.

In one embodiment, the present subject matter provides for a system and a method in which one or more cardiac signals are sensed and analyzed during a tachycardia episode to classify primary and auxiliary depolarizations occurring during the episode as either associated or disassociated. In one embodiment, the primary and auxiliary depolarizations are any combination of atrial depolarizations and/or ventricular depolarizations.

During the tachycardia episode, a first time interval is positioned to surround each of one or more primary depolarizations. In addition to surrounding the one or more primary depolarizations, the first time interval also surrounds auxiliary depolarizations that occur in the first time interval. The auxiliary depolarizations occurring in the first time interval are then counted. Based on the number and the location of the auxiliary depolarizations counted in the first time intervals, the one or more primary depolarizations and the auxiliary depolarizations of the tachycardia episode are classified as disassociated or associated.

In one embodiment, the first time interval is a calculated from an average value ($XX_{avg}$) and a standard deviation value ($XX_{sd}$) of auxiliary cycle lengths measured between pairs of consecutively sensed auxiliary depolarizations in a measurement window interval. The first time interval is calculated using the formula ($XX_{avg}-Y*XX_{sd}$) where Y is a predetermined constant. In one embodiment, the auxiliary cycle lengths that were sensed and analyzed during the tachycardia episode to determine the first time interval and the associated primary depolarizations sensed during the measurement window interval are analyzed to determine whether the tachycardia episode is associated or disassociated.

In one embodiment, classifying the tachycardia episode as associated or disassociated includes counting a first number (K) of auxiliary depolarizations during a first-half of the first time interval for each of the one or more primary depolarizations. In addition to counting the first number (K), a total number (N) of auxiliary depolarizations are counted during the first time interval for each of the one or more primary depolarizations. A K/N value is then calculated and the one or more primary depolarizations and the auxiliary depolarizations of the tachycardia episode are then classified as disassociated or associated based on K/N. Alternatively, K is compared to threshold values $K_{low}$ and $K_{high}$ to classify the primary and auxiliary depolarizations, where the primary and auxiliary depolarizations are classified as associated when K is less than or equal to $K_{low}$ or greater than or equal to $K_{high}$, and the primary and auxiliary depolarizations are classified as disassociated when K is between $K_{low}$ and $K_{high}$.

In addition to using a first time interval in classifying the tachycardia episode, a second time interval can also be used to surround each of one or more auxiliary depolarizations of the auxiliary depolarizations, where the second time interval surrounds primary depolarizations that occur in the second time interval. A first number of primary depolarizations are then counted during a first-half of the second time interval for the one or more auxiliary depolarizations. A total number of primary depolarizations are also counted during the second time interval for each of the one or more auxiliary depolarizations. Based on the first number of auxiliary depolarizations, the total number of auxiliary depolarizations, the first number of primary depolarizations and the total number of primary depolarizations a classification of the tachycardia episode is made. In one embodiment, once the classification is made, additional analysis procedures can be better directed in analyzing the tachycardia episode. In turn, this could lead to more appropriate therapy being used to treat the tachycardia episode.

These and other features and advantages of the invention will become apparent from the following description of the preferred embodiments of the invention.

DETAILED DESCRIPTION

In the following detailed description, references are made to the accompanying drawings that illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

The present subject matter is useful in determining whether atrial and ventricular contractions, or depolarizations, are associated or disassociated. Atrial and ventricular depolarizations that are associated indicate that an activation event occurring in one chamber causes a subsequent activation event in the other chamber. In other words, there is conduction of the cardiac activation event from one chamber to the other chamber. Atrial and ventricular depolarizations that are disassociated indicate that activation events that occur in one chamber do not have a recognized effect on an activation event that occurs in the other chamber.

One situation where classifying atrial and ventricular contractions of a tachycardia episode as being either associated or disassociated is in the discrimination, or classification, of ventricular tachycardia episodes from supraventricular tachycardia episodes. The ability to accurately classify a ventricular tachycardia episode from a supraventricular tachycardia episode allows the mechanism of the tachycardia episode to be identified which helps greatly in directing appropriate therapy.

The present subject matter relies on sensed atrial depolarizations and sensed ventricular depolarizations in classifying a tachycardia episode. In one embodiment, a time interval "window" is positioned to surround ventricular and atrial cardiac complexes detected in one or more cardiac signals sensed during a tachycardia episode, where the one or more cardiac signals include indications of ventricular depolarizations and atrial depolarizations. In one embodiment, the time interval "window" can be envisioned as a box that surrounds cardiac complexes indicating ventricular depolarizations and cardiac complexes indicating atrial depolarizations. The number of atrial depolarizations and/or the number of ventricular depolarizations within the time intervals surrounding the cardiac complexes are then counted. Based on the number depolarizations counted in the time intervals surrounding the atrial depolarizations and/or the ventricular depolarizations, of the tachycardia episode is classified as either disassociated or associated.

Figure 1:
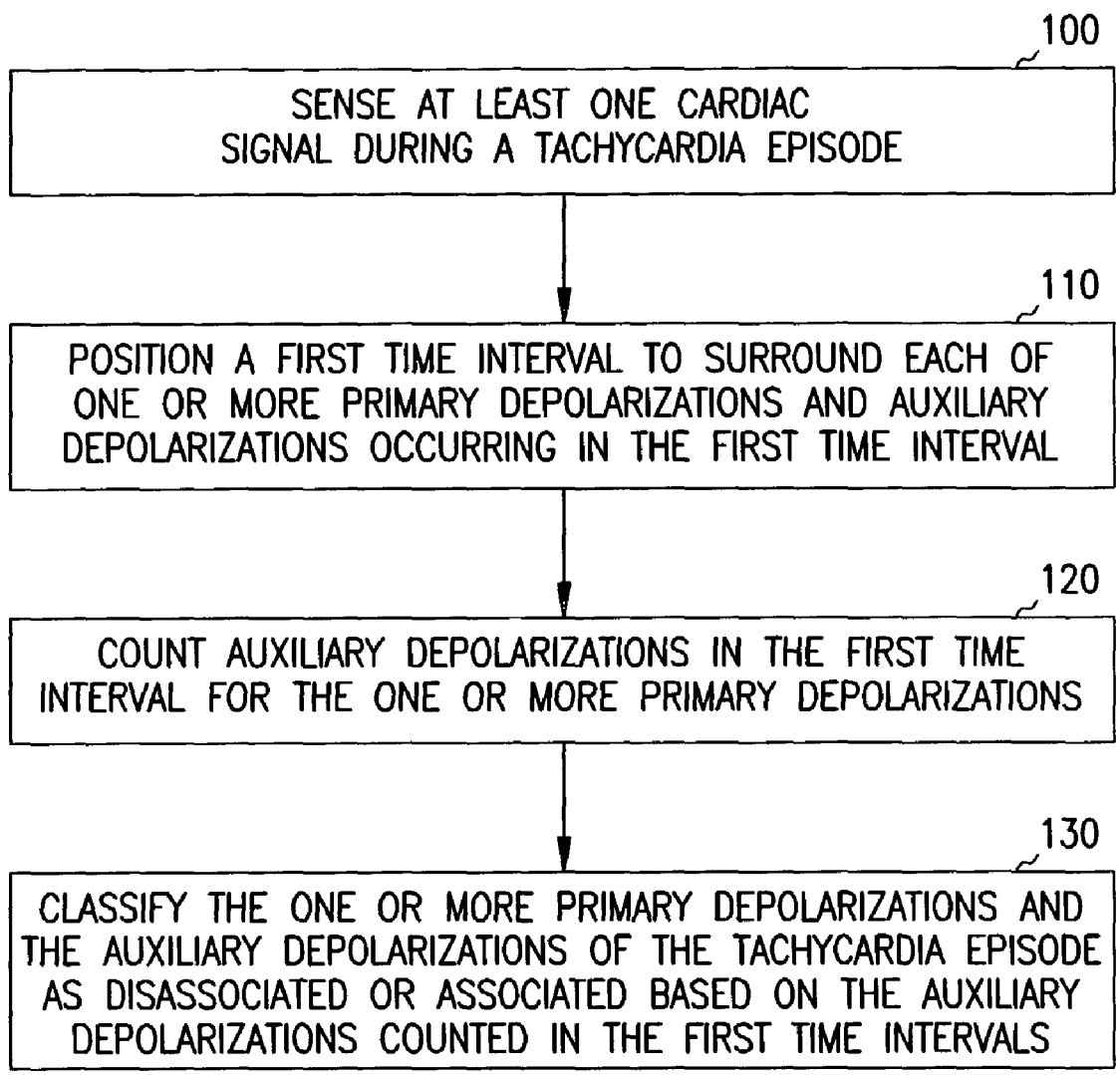
FIG. 1 is a flow chart illustrating one embodiment of the present subject matter.

Referring now to FIG. 1, there is shown one embodiment of a method for the present subject matter. At 100, at least one cardiac signal is sensed, where the at least one cardiac signal includes primary depolarizations and auxiliary depolarizations. In one embodiment, the primary depolarizations and auxiliary depolarizations can be any combination of atrial depolarizations and/or ventricular depolarizations sensed during a tachycardia episode, as will be more fully discussed below. In one embodiment, the tachycardia episode is a non-normal sinus episode. For example, the tachycardia episode can be a ventricular arrhythmia having its origins in either a supraventricular region (e.g., a supraventricular tachycardia) or a ventricular region (e.g., a ventricular tachycardia) of the heart. Alternatively, the tachycardia episode can be a supraventricular arrhythmia having its origins in either the ventricular region or supraventricular region of the heart. The tachycardia episode can also be a dual arrhythmia, where both ventricular and supraventricular arrhythmias are present at the same time, but are not associated with each other.

In one embodiment, sensing at least one cardiac signal includes sensing, or receiving, a first cardiac signal and a second cardiac signal during the tachycardia episode. The first cardiac signal includes indications of depolarizations in a first cardiac area and the second cardiac signal includes indications of depolarizations in a second cardiac area, where in one embodiment the first cardiac signal includes primary depolarizations and the second cardiac signal includes auxiliary depolarizations.

At 110, a first time interval is positioned to surround each of one or more primary depolarizations of the primary depolarizations, where the time interval also surrounds auxiliary depolarizations that occur in the time interval. Thus, the time interval surrounds both a primary depolarization of the one or more primary depolarizations and the auxiliary depolarizations that occur during the duration of the time interval.

At 120, the auxiliary depolarizations that occurred during the time interval are then counted for the one or more primary depolarizations. At 130, the one or more primary depolarizations and the auxiliary depolarizations of the tachycardia episode are then classified as either being disassociated or associated based on the auxiliary depolarizations counted in the first time interval for the one or more primary depolarizations. In one embodiment, the number of auxiliary depolarizations that occur during a first portion of the first time interval that surrounds each of one or more primary depolarizations and the number of auxiliary depolarizations that occur during a second portion of the first time interval are used to classify the primary and auxiliary depolarizations of the tachycardia episode as either associated or disassociated.

Figure 2:
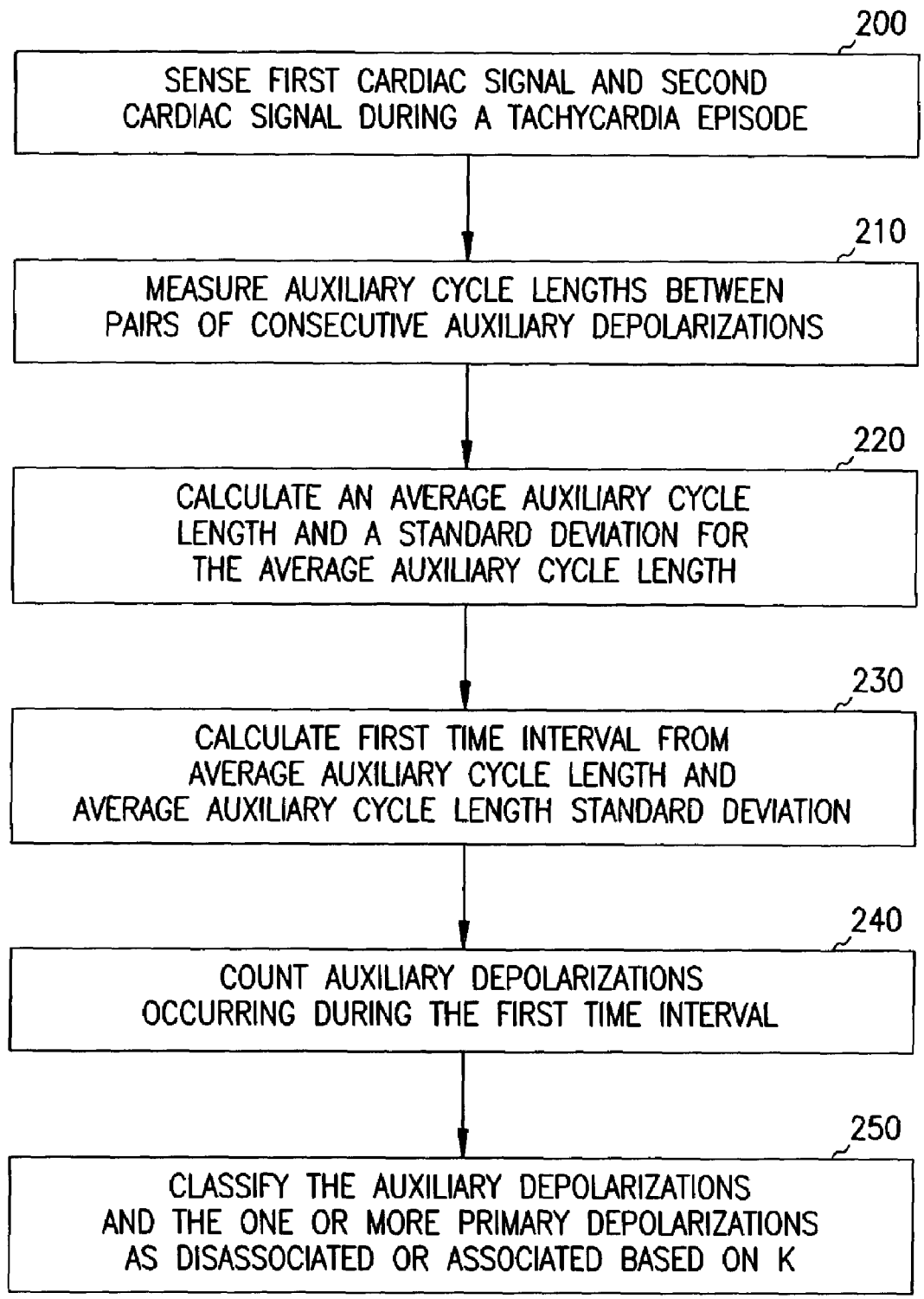
FIG. 2 is a flow chart illustrating one embodiment of the present subject matter.

Referring now to FIG. 2, there is shown an additional embodiment of the present subject matter. At 200, a first cardiac signal and a second cardiac signal are sensed. In one embodiment, the first cardiac signal includes the primary depolarizations and the second cardiac signal includes the auxiliary depolarizations, where the primary depolarizations are sensed in the first cardiac signal and the auxiliary depolarizations are sensed in the second cardiac signal.

At 210, auxiliary cycle lengths are measured between pairs of consecutive sensed auxiliary depolarizations sensed during the tachycardia episode. In one embodiment, the auxiliary cycle length is the time interval between two consecutively sensed cardiac depolarizations (e.g., atrial depolarizations or ventricular depolarizations), where the measurement is made at the same relative position of the auxiliary depolarization along the cardiac signal. In addition to measuring the auxiliary cycle lengths, the auxiliary depolarization rate is also calculated and recorded for use with the present subject matter.

In one embodiment, the auxiliary cycle lengths and auxiliary depolarization rate are measured during a measurement window interval. In one embodiment, the measurement window interval can be programmed with a predetermined duration, where in one embodiment the predetermined duration is in a range of 5 to 60 seconds, where 10 seconds can be used. Alternatively, the duration of the measurement window interval is dependent upon the number of sensed primary, or auxiliary, depolarizations. For example, a predetermined number of primary depolarizations can be programmed (e.g., 20 primary depolarizations) that define the duration of the measurement window interval, where once the predetermined number of primary depolarizations have been sensed the measurement window interval is stopped.

In one embodiment, as the auxiliary cycle lengths in the window interval are measured, or calculated, they are used at 220 to calculate an average value ($XX_{avg}$) and a standard deviation value ($XX_{sd}$) of the auxiliary cycle lengths for the consecutively sensed auxiliary depolarizations in the measurement window interval. In one embodiment, the $XX_{avg}$ and the $XX_{sd}$ are calculated for each subsequent auxiliary depolarization as they are sensed.

In an alternative embodiment, the values of $XX_{avg}$ and the $XX_{sd}$ are calculated from a predetermined number of consecutively sensed auxiliary depolarizations, where up-dated values of $XX_{avg}$ and the $XX_{sd}$ are calculated from the predetermined number of sensed auxiliary depolarizations as each subsequent auxiliary depolarization is sensed in the measurement window interval. In one embodiment, the predetermined number of consecutively sensed auxiliary depolarizations has a value of at least 3 consecutive auxiliary depolarizations. Alternatively, the predetermined number of consecutively sensed auxiliary depolarizations is a programmable number in the range of 3 to 50 depolarizations, where 10 depolarizations is an acceptable number.

At 230, once the $XX_{avg}$ and the $XX_{sd}$ are calculated, the first time interval is then calculated. In one embodiment, the first time interval has a value equal to:

$$(XX_{avg} - Y \ast XX_{sd})$$

where Y is a predetermined constant. In one embodiment, Y is a programmable value in the range of 0.0 to 5.0, where 1.0 is a value that can be used.

In one embodiment, in addition to sensing and analyzing the auxiliary depolarizations to determine the first time interval, the primary depolarizations are also sensed and analyzed for the presence of a tachycardia episode. In one embodiment, the presence of a tachycardia episode is determined through the use of a rate threshold criteria as is known. Once a tachycardia episode has been identified from the primary depolarizations, the first time interval is positioned to surround each of one or more primary depolarizations of the primary depolarizations. In addition to surrounding each of the one or more primary depolarizations, the time interval also surrounds the auxiliary depolarizations in the second cardiac signal that occurred during the same relative time as each of the one or more primary depolarization in the first cardiac signal.

Figure 3:
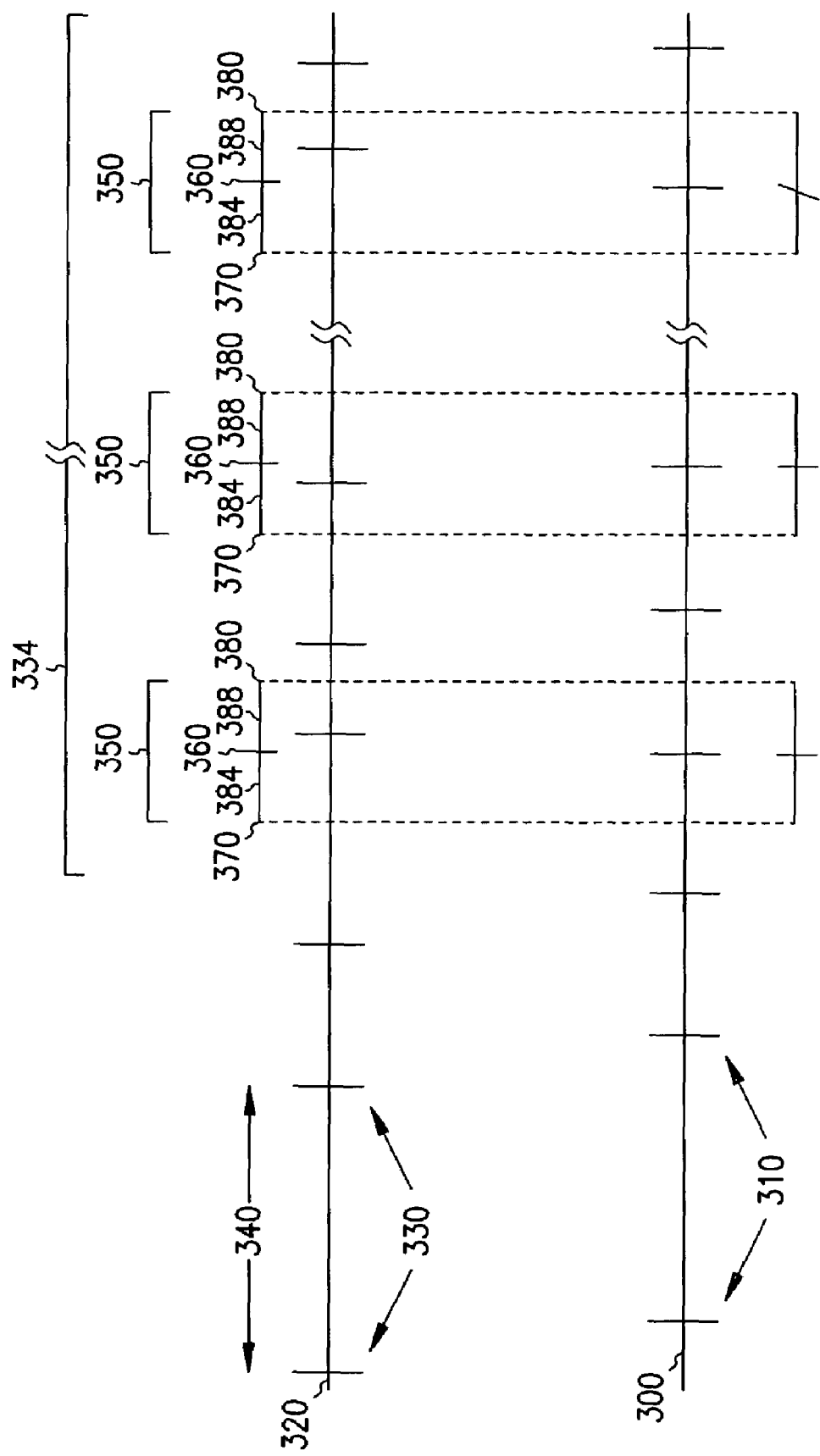
FIG. 3 is an illustration of one embodiment of a first cardiac signal and a second cardiac signal according to the present subject matter.

Referring now to FIG. 3, there is shown an embodiment of a first time interval positioned to surround one or more primary depolarizations and auxiliary depolarizations. A first cardiac signal is shown at 300, where the first cardiac signal 300 shows indications of primary depolarizations at 310. A second cardiac signal is shown at 320, where the second cardiac signal 320 shows indications of auxiliary depolarizations at 330. As previously discussed, auxiliary cycle lengths are measured between auxiliary depolarizations 330 consecutively sensed during a measurement window interval 334, where an example of an auxiliary cycle length is shown at 340. Once a tachycardia episode is detected a first time interval calculated from the sensed auxiliary depolarizations 330 is positioned to surround one or more primary depolarizations 310 that occur during the tachycardia episode. In one embodiment, the first time interval surrounds the depolarizations that were sensed during the measurement window interval 334. An example of the first time interval surrounding one or more primary depolarizations 310 and auxiliary depolarizations 330 is shown generally at 350.

In an additional embodiment, the first time interval 350 includes a midpoint location 360 having a start point 370 and an end point 380 of the first time interval 350. In one embodiment, the midpoint location 360 of the first time interval 350 is positioned, or situated, at the primary depolarization 310 of each of the one or more primary depolarizations (e.g., the midpoint 360 is positioned with the primary depolarization 310 between the start point 370 and the end point 380 of the first time interval). When the first time interval 350 is positioned with the primary depolarization 310 at the midpoint 360, there is a first-half 384 and a second-half 388 of the first time interval 350, where the first-half 384 of the first time interval 350 precedes the midpoint location 360 and the second-half 388 of the first time interval 350 follows, or is subsequent, to the midpoint location 360.

In one embodiment, the first-half 384 and the second-half 388 of the first time interval have values which are calculated from the equation $(XX_{avg} - Y \ast XX_{sd})/2$, where Y is the predetermined constant previously discussed. In one embodiment, for each primary depolarization (e.g., each sensed R-wave, QRS-complex, or P-wave) the first cardiac signal is examined to count sensed auxiliary depolarizations (e.g., R-waves, QRS-complexes, or P-waves) that occurred in the first-half of the first time interval and in the second-half of the time interval.

In one embodiment, the first time interval is positioned to surround consecutive primary depolarizations of the one or more primary depolarizations. Alternatively, the first time interval is positioned to surround one or more primary depolarizations meeting a predetermined selection criteria. In an additional embodiment, the first time interval is positioned to surround the one or more primary depolarizations that occur during a predetermined period of time. Additionally, the first time interval is positioned to surround the one or more primary depolarizations until a predetermined number of the one or more primary depolarizations is reached. In an additional embodiment, the first time interval is positioned to surround the one or more primary depolarizations until a predetermined statistical criteria is reached.

Referring again to FIG. 2, once the first time interval have been positioned to surround each of the one or more primary depolarizations, the auxiliary depolarizations occurring in the first time interval are counted at 240. In one embodiment, a total number (N) of auxiliary depolarizations that appear in the first time intervals surrounding each of the one or more primary depolarizations are counted. In addition to counting the total number (N) of auxiliary depolarizations, a first number of auxiliary depolarizations (K) occurring in the first-half of the first time interval for each of the one or more primary depolarizations is also counted at 240.

At 250, the one or more primary depolarizations and the auxiliary depolarizations are then classified as either associated or disassociated based on the first number of auxiliary depolarizations (K) an the total number of auxiliary depolarizations (N). For example, in one embodiment the values of N and K are used to calculate K/N. The auxiliary depolarizations and the one or more primary depolarizations of the tachycardia episode are then classified as disassociated or associated based on the value of K/N.

In one embodiment, the value of K/N can be used to determine whether auxiliary and one or more primary depolarizations are associated or disassociated based on the probability of the auxiliary depolarizations occurring before or after the occurrence of a primary depolarization. For example, if the auxiliary depolarizations were atrial depolarizations and the primary depolarizations were ventricular depolarizations, and if the atrial and ventricular depolarizations were not associated in any way, the atrial depolarizations would have uniform probability of appearing in either the first-half or second-half of the time interval. In that case, the total count for both the first-half of the time interval and the second-half of the time interval would be about the same (i.e., K/N would be equal to approximately one-half (0.5)). Thus, the one or more primary depolarizations and the auxiliary depolarizations of the tachycardia episode would be classified as disassociated when K/N is equal to approximately one-half (0.5).

On the other hand, if atrial depolarizations were conducted to the ventricles and thus were responsible for the ventricular depolarizations, or if ventricular depolarizations were conducted to the atria and thus were responsible for the atrial depolarization, then the relationship between the timings of the atrial and ventricular depolarizations would not be random. Rather, the atrial depolarizations would either consistently appear in the first half of the time intervals, but not the second half, so that K/N would be greater than one-half (0.5); or atrial depolarizations would consistently appear in the second half of the time intervals, but not the first half, so that K/N would be less than one-half (0.5). Thus, the one or more primary depolarizations the auxiliary depolarizations of the tachycardia episode would be classified as associated when K/N is not equal to approximately one-half (0.5).

In an additional embodiment, the primary and auxiliary depolarizations are classified as associated if K/N is between 0.5−X and 0.5+X. Similarly, the primary and auxiliary depolarizations are classified as disassociated if K/N is outside the range from 0.5−X to 0.5+X. Here, X is a predetermined and programmable number ranging from 0.0 to 0.5, where 0.1 is an acceptable value.

In a further embodiment, the value of K/N is tested to determine if the ratio is different from 0.5 or if the calculated value of K/N could occur by chance alone. The following statistic has a standard normal distribution:

$$\frac{(K/N - 0.5)}{[K/N \ast (1 - K/N)/N]^{1/2}}$$

If this statistic is greater than a critical value Zcrit (determined by the desired confidence in the classification) then the ratio K/N is different from one-half (0.5). Since K/N can be either lower or higher than one-half (0.5), this condition can be met either when K is less than a lower critical value ($K \leq K_{low}$) or when K is greater than a higher critical value ($K \leq K_{high}$). These critical values are computed from the number N and the desired Zcrit as follows:

$$K_{low} = N/2[1-(1+N/Zcrit)^{-1/2}]$$

$$K_{high} = N/2[1+(1+N/Zcrit)^{-1/2}]$$

For a 95% confidence in the classification, a Zcrit equal to 1.96 is used. For a 99% confidence in the classification, a Zcrit equal to 2.58 is used.

Then, the auxiliary depolarizations and the one or more primary depolarizations are classified as associated when K/N is statistically different from one-half (0.5) at the predetermined confidence level. That is, when K is less than or equal to $K_{low}$ or when K is greater than or equal to $K_{high}$. Alternatively, the auxiliary depolarizations and the one or more primary depolarizations are classified as disassociated when K/N is not statistically different from one-half (0.5) at the predetermined confidence level. That is, when K is between $K_{low}$ and $K_{high}$. In one embodiment, the predetermined confidence level is the 95 percent (%) confidence level. Alternatively, the predetermined confidence level is the 99 percent (%) confidence level.

In an additional embodiment, K and the threshold values $K_{low}$ and $K_{high}$ can be used to ensure the measurement window interval is of sufficient duration to provide primary and auxiliary depolarizations that are classified with a predetermined confidence level. For example, K is compared to threshold values $K_{low}$ and $K_{high}$ to determine when primary and auxiliary depolarizations are classified with a predetermined confidence level. When the primary and auxiliary depolarizations are not classified with a predetermined confidence level, the measurement window interval is extended in duration until a fixed confidence level is reached. In one embodiment, the measurement window interval is repeated when the relationship of K to threshold values $K_{low}$ and $K_{high}$ shows that primary and auxiliary depolarizations are not classified with the predetermined confidence level. Alternatively, the measurement window interval is stopped when the relationship of K to threshold values $K_{low}$ and $K_{high}$ shows that primary and auxiliary depolarizations are classified with the predetermined confidence level.

In an additional embodiment, besides counting the first number of auxiliary depolarizations (K) occurring in the first-half of the first time interval for each of the one or more primary depolarizations, a second number of auxiliary depolarizations (J) in the second-half of the first time interval for the one or more primary depolarizations, and determining whether the first number and the second number are statistically different at a predetermined confidence level, where an example of the predetermined confidence level is as previously described. In one embodiment, the one or more primary depolarizations and the auxiliary depolarizations are classified as associated when the number of auxiliary depolarizations in the first-half of the first time interval (K) and the second-half of the first time interval (J) for the one or more primary depolarizations are statistically different at the predetermined confidence level. Alternatively, the one or more primary depolarizations and the auxiliary depolarizations are classified as disassociated when the number of auxiliary depolarizations in the first-half of the first time interval (K) and the second-half of the first time interval (J) for the one or more primary depolarizations are not statistically different at the predetermined confidence level.

In an alternative embodiment, in addition to computing a first time interval based on the auxiliary depolarizations and positioning the first time intervals to surround each of the one or more primary depolarizations, a second time interval can also be computed based on primary depolarizations where the second time interval is positioned to surround each of one or more auxiliary depolarizations and the primary depolarizations that occur within the second time interval are counted and used either alone or in conjunction with the auxiliary depolarizations counted within the first time interval. In one embodiment, the second time interval is calculated in the same manner as the first time interval.

Figure 4:
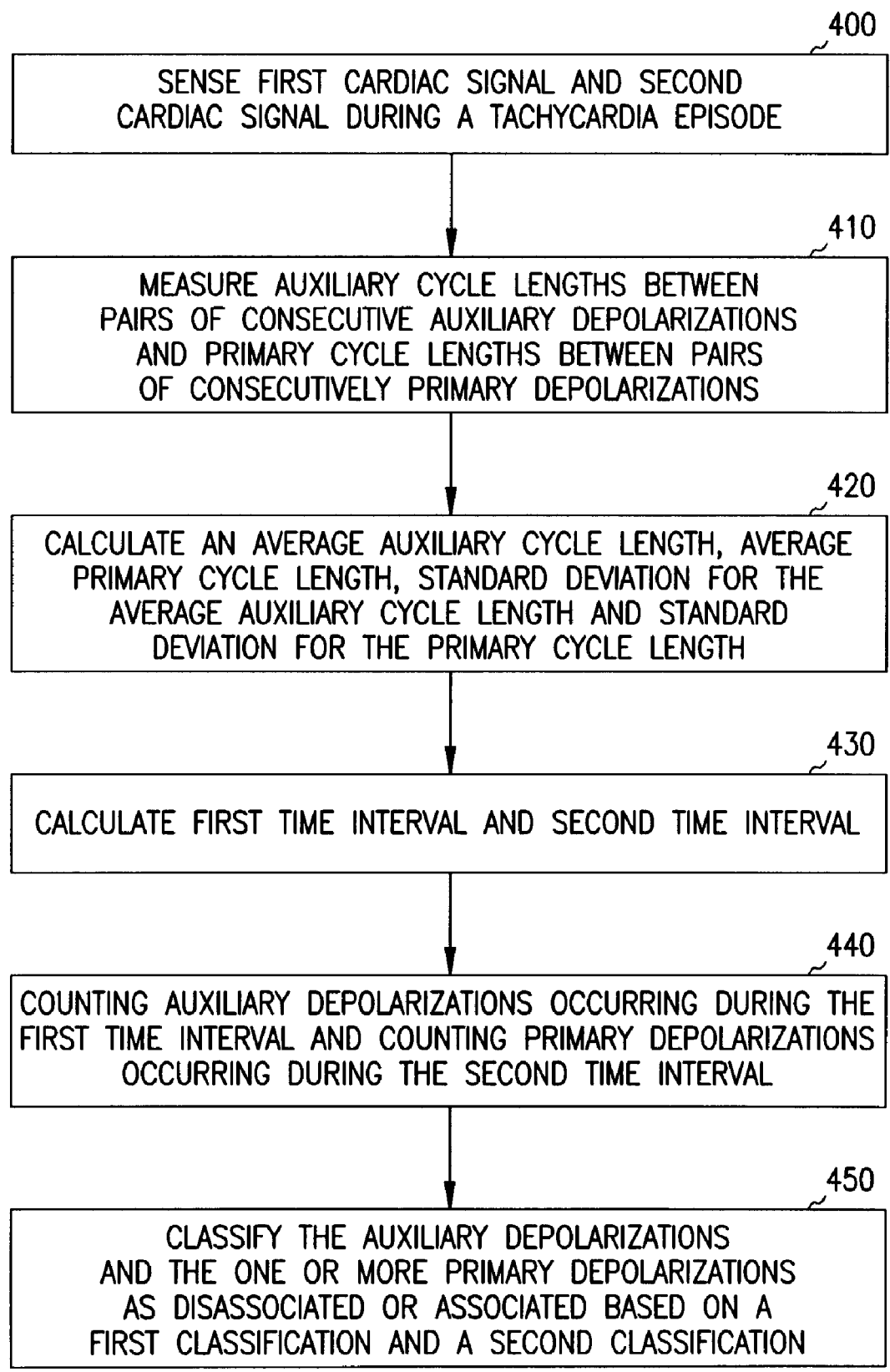
FIG. 4 is a flow chart illustrating one embodiment of the present subject matter.

Referring now to FIG. 4, there is shown an additional embodiment of the present subject matter. At 400, a first cardiac signal and a second cardiac signal are sensed. In one embodiment, the first cardiac signal includes the primary depolarizations and the second cardiac signal includes the auxiliary depolarizations, where the primary depolarizations are sensed in the first cardiac signal and the auxiliary depolarizations are sensed in the second cardiac signal.

At 410, auxiliary cycle lengths are measured between pairs of consecutively sensed auxiliary depolarizations (as previously described) and primary cycle lengths are measured between pairs of consecutive sensed primary depolarizations sensed during the tachycardia episode. In one embodiment, the primary cycle length is the time interval between two consecutively sensed cardiac depolarizations (e.g., atrial depolarizations or ventricular depolarizations), where the measurement is made at the same relative position of the primary depolarization along the cardiac signal. In addition to measuring the primary cycle lengths, the primary depolarization rate is also calculated and recorded for use with the present subject matter.

In one embodiment, the primary cycle lengths and primary depolarization rate are measured during the measurement window interval. In one embodiment, the measurement window interval can be programmed with a predetermined duration, where in one embodiment the predetermined duration is in a range of 5 to 60 seconds, where 10 seconds can be used. Alternatively, the duration of the measurement window interval is dependent upon the number of sensed primary, or auxiliary, depolarizations. For example, a predetermined number of auxiliary depolarizations can be programmed (e.g., 20 auxiliary depolarizations) that define the duration of the measurement window interval, where once the predetermined number of auxiliary depolarizations have been sensed the measurement window interval is stopped.

At 420, as the primary cycle lengths in the window interval are measured, or calculated, they are used to calculate the average value ($XX_{avg}$) and the standard deviation value ($XX_{sd}$) of the primary cycle lengths for the consecutively sensed primary depolarizations in the measurement window interval. In one embodiment, the $XX_{avg}$ and the $XX_{sd}$ are calculated for each subsequent primary depolarization as they are sensed. An average value and standard deviation value of the auxiliary cycle lengths for consecutively sensed auxiliary depolarizations in the measurement window interval are also calculated as previously described.

In an alternative embodiment, the values of $XX_{avg}$ and the $XX_{sd}$ are calculated from a predetermined number of consecutively sensed primary depolarizations, where up-dated values of $XX_{avg}$ and the $XX_{sd}$ are calculated from the predetermined number of sensed primary depolarizations as each subsequent primary depolarization is sensed in the measurement window interval. In one embodiment, the predetermined number of consecutively sensed primary depolarizations has a value of at least 3 consecutive primary depolarizations. Alternatively, the predetermined number of consecutively sensed primary depolarizations is a programmable number in the range of 3 to 50 depolarizations, where 10 depolarizations is an acceptable number.

At 430, once the $XX_{avg}$ and the $XX_{sd}$ for the primary and auxiliary depolarizations are calculated, the first time interval and the second time interval are calculated. In one embodiment, the first and second time intervals each have an individual value which is calculated by the equation:

$$(XX_{avg} - Y*XX_{sd})$$

where Y is a predetermined constant for each of the first and second time intervals. In one embodiment, Y is a programmable value in the range of 0.0 to 5.0, where 1.0 is a value that can be used.

In one embodiment, in addition to sensing and analyzing the auxiliary depolarizations and the primary depolarizations to determine the first time interval and the second time interval, the primary depolarizations and/or the auxiliary depolarizations are sensed and analyzed for the presence of a tachycardia episode as previously described. Once a tachycardia episode has been identified, the first time interval is positioned to surround each of one or more primary depolarizations of the primary depolarizations and the second time interval is positioned to surround each of one or more auxiliary depolarizations of the auxiliary depolarizations. Analysis of both the auxiliary and the primary depolarizations within the first and second time intervals is then used to classify the tachycardia episode as either associated or disassociated.

At 440, for the first time intervals that surround the one or more primary depolarizations, the first number (K) of the auxiliary depolarizations that occur in the first-half of any of the first time intervals is counted for each of the one or more primary depolarizations. Also, the total number (N) of auxiliary depolarizations that occur anywhere in any of the first time intervals is counted for each of the one or more primary depolarizations. Further, for the second time intervals that surround the one or more auxiliary depolarizations, a first number (L) of primary depolarizations that occur in the first-half of any of the second time interval for the one or more auxiliary depolarizations is counted. Still further, a total number (M) of primary depolarizations that occur during the second time interval for the one or more auxiliary depolarizations is counted for each of the one or more auxiliary depolarizations.

At 450, the tachycardia episode classified as disassociated or associated based on a first classification and a second classification of the auxiliary depolarizations and the primary depolarizations. In one embodiment, the first classification of the one or more primary depolarizations and the one or more auxiliary depolarizations of the tachycardia episode as either associated or disassociated is based on K and N. Additionally, the second classification of the one or more primary depolarizations and the one or more auxiliary depolarizations of the tachycardia episode as either associated or disassociated is made based on L and M. In one embodiment, the first number and second number of primary depolarizations are processed in a manner similar to that described for the first and second number of the auxiliary depolarization, to determine the second classification of whether the auxiliary depolarizations and the one or more primary depolarizations are either associated or disassociated.

In one embodiment, the primary and auxiliary depolarization of the tachycardia episode are classified as associated when both the first classification and the second classification are classified as associated. In one embodiment, the primary and auxiliary depolarization of the tachycardia episode are classified as disassociated when both the first classification and the second classification are classified as disassociated. In an alternative embodiment, the primary and auxiliary depolarization of the tachycardia episode are classified as disassociated when either the first classification or the second classification are classified as disassociated. Alternatively, the primary and auxiliary depolarization of the tachycardia episode are classified as associated when either the first classification or the second classification are classified as associated. In one embodiment, the primary and auxiliary depolarization are classified as associated if the first classification and the second classifications are different and the one with the higher statistical significance is associated. In an additional embodiment, a statistical significance is calculated for each of the first classification and the second classification. The classification of the tachycardia episode is then based on when the first classification and the second classification have different classifications. For example, the tachycardia episode is classified as associated when the first classification and the second classification have different classifications and the associated classification has a higher statistical significance than the disassociated classification. Alternatively, the tachycardia episode is classified as disassociated when the first classification and the second classification have different classifications and the disassociated classification has a higher statistical significance than the associated classification.

Figure 5:
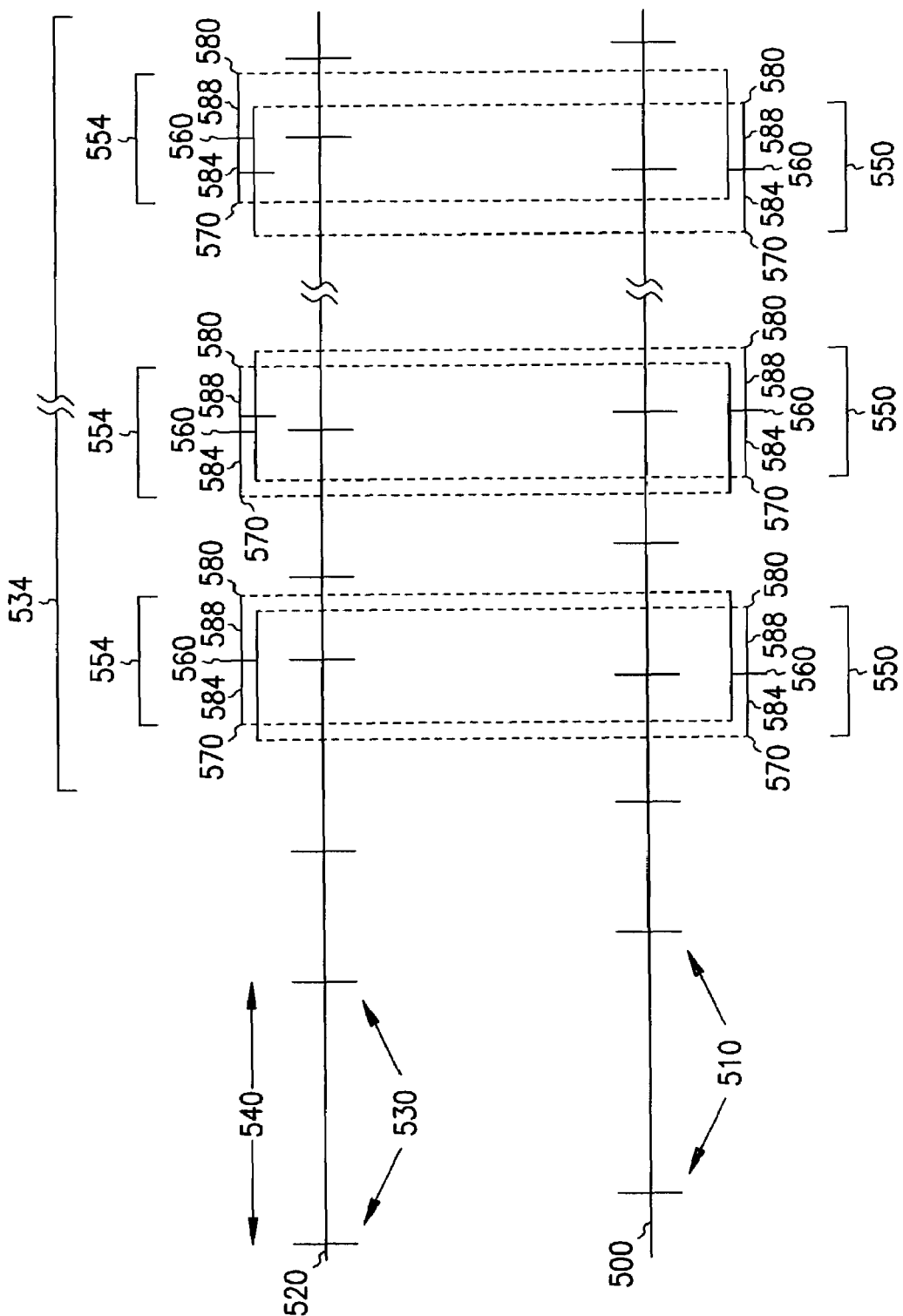
FIG. 5 is an illustration of one embodiment of a first cardiac signal and a second cardiac signal according to the present subject matter.

Referring now to FIG. 5, there is shown an embodiment of a first time interval and a second time interval positioned to surround primary depolarizations and auxiliary depolarizations. A first cardiac signal is shown at 500, where the first cardiac signal 500 shows indications of primary depolarizations at 510. A second cardiac signal is shown at 520, where the second cardiac signal 520 shows indications of auxiliary depolarizations at 530. As previously discussed, auxiliary cycle lengths are measured between auxiliary depolarizations 530 consecutively sensed in a measurement window interval 534 during a tachycardia episode, where an example of an auxiliary cycle length is shown at 540. Primary cycle lengths are measured between primary depolarizations 510 consecutively sensed in the measurement window interval.

Once the tachycardia episode is detected the first time interval calculated from the sensed auxiliary depolarizations 530 and the second time interval are positioned to surround the primary depolarizations 510 and the auxiliary depolarizations 530 that occur during the tachycardia episode. In one embodiment, the first time intervals and the second time intervals surround the depolarizations that were sensed during the measurement window interval 534. An example of the first time interval surrounding one or more primary depolarizations 510 and auxiliary depolarizations 530 is shown generally at 550, and an example of the second time interval surrounding one or more auxiliary depolarizations 530 and primary depolarizations 510 is shown generally at 554.

In an additional embodiment, both the first time interval 550 and the second time interval 554 includes a midpoint location 560 having a start point 570 and an end point 580. In one embodiment, the midpoint location 560 of the first time interval 550 is positioned, or situated, at the primary depolarization 510 of each of the one or more primary depolarizations (e.g., the midpoint 560 is positioned with the ventricular depolarization 510 between the start point 570 and the end point 580 of the first time interval). When the first time interval 550 is positioned with the primary depolarization 510 at the midpoint 560, there is a first-half 584 and a second-half 588 of the first time interval 550, where the first-half 584 of the first time interval 550 precedes the midpoint location 560 and the second-half 588 of the first time interval 550 follows, or is subsequent, to the midpoint location 560.

In one embodiment, the midpoint location 560 of the second time interval 554 is positioned, or situated, at the auxiliary depolarization 530 of each of the one or more auxiliary depolarizations (e.g., the midpoint 560 is positioned with the auxiliary depolarization 530 between the start point 570 and the end point 580 of the second time interval). When the second time interval 554 is positioned with the auxiliary depolarization 530 at the midpoint 560, the first-half 584 of the first time interval 550 precedes the midpoint location 560 and the second-half 588 of the first time interval 550 follows, or is subsequent, to the midpoint location 560.

In one embodiment, the first time interval is positioned to surround consecutive primary depolarizations of the one or more primary depolarizations and the second time interval is positioned to surround consecutive auxiliary depolarizations of the one or more auxiliary depolarizations. Alternatively, the first time interval and the second time interval are positioned to surround their respective depolarizations that meet a predetermined selection criteria. In an additional embodiment, the first time interval and the second time interval are positioned to surround their respective depolarizations that occur during a predetermined period of time. Additionally, the first time interval and the second time interval are positioned to surround their respective depolarizations until a predetermined number of the one or more primary depolarizations and/or the one or more auxiliary depolarizations is reached. In an additional embodiment, the first time interval and the second time interval are positioned to surround their respective depolarizations until a predetermined statistical criteria is reached.

Currently, implanted rhythm management devices use a similarity in atrial and ventricular rates (for example, atrial and ventricular rates equal to within 10%) to assess if depolarization in the atrial and ventricular chambers are associated. One use for the determination methods described herein is to confirm the primary assessment that is based on rates alone. Alternatively, the association/disassociation determination described herein could replace the use of rates as the primary determination. Another use for the association/disassociation determination described herein is to confirm the existence of sinus tachycardia (ST) since a ST would require both an association of atrial and ventricular depolarization and equal rates. Yet another use for the association/disassociation determination described herein is to identify cases of dual tachycardias (simultaneous atrial and ventricular tachycardias) that have similar rates since dual tachycardias are not associated. A further use for the association/disassociation determination described herein is as a gatekeeper for algorithms designed to distinguish between antegrade and retrograde conduction in one-to-one tachycardias. Such algorithms require a strong association between atrial and ventricular depolarizations so that they distinguish ST from ventricular tachycardia with retrograde conduction. By restricting those algorithms for use only in rhythms classified as associated by the methods described herein, their validity is improved.

In one embodiment, the auxiliary and primary depolarizations of the present subject matter are any combination of sensed atrial depolarizations and/or ventricular depolarizations. Thus, both the auxiliary and the primary depolarizations could be sensed from a first cardiac area and a second cardiac area both located in the supraventricular region of the heart. Alternatively, the auxiliary and the primary depolarizations could be sensed from a first cardiac area and a second cardiac area both located in the ventricular region of the heart. Additionally, the auxiliary depolarizations could be sensed from a first cardiac area in the supraventricular region of the heart and the primary depolarizations could be sensed from a second cardiac area in the ventricular region of the heart, or the primary depolarizations could be sensed from a first cardiac area in the supraventricular region of the heart and the auxiliary depolarizations could be sensed from a second cardiac area in the ventricular region of the heart.

In one embodiment, the atrial depolarizations are sensed across the supraventricular region of a heart, where one or more electrodes are positioned within, on, or around the supraventricular region of the heart. Electrode structures suitable for implantation in the supraventricular region that allow for either unipolar or bipolar signals to be sensed for the first cardiac signal are known. In one embodiment, the atrial depolarizations sensed in a cardiac signal (such as either the first or second cardiac signal) are P-waves created from the depolarizations of one or more of the atrial chambers. In an additional embodiment, the ventricular depolarizations are sensed across at least a ventricular region of the heart, where one or more electrodes located within, on, or around the ventricular region of the heart. Electrode structures suitable for implantation in the ventricular region that allow for either unipolar or bipolar signals to be sensed for the first cardiac signal are known. In one embodiment, the ventricular depolarizations sensed are R-waves detected from the depolarizations of one or more of the ventricular chambers. In one embodiment, the R-waves are detected with electrodes adapted to sense rate signals (or near-field signals). Alternatively, the ventricular depolarizations sensed in the second cardiac signal are QRS-complexes detected from the depolarizations of one or more of the ventricular chambers. In one embodiment, the QRS-complexes are detected with electrodes adapted to sense morphology signals (or far-field signals).

Figure 6:
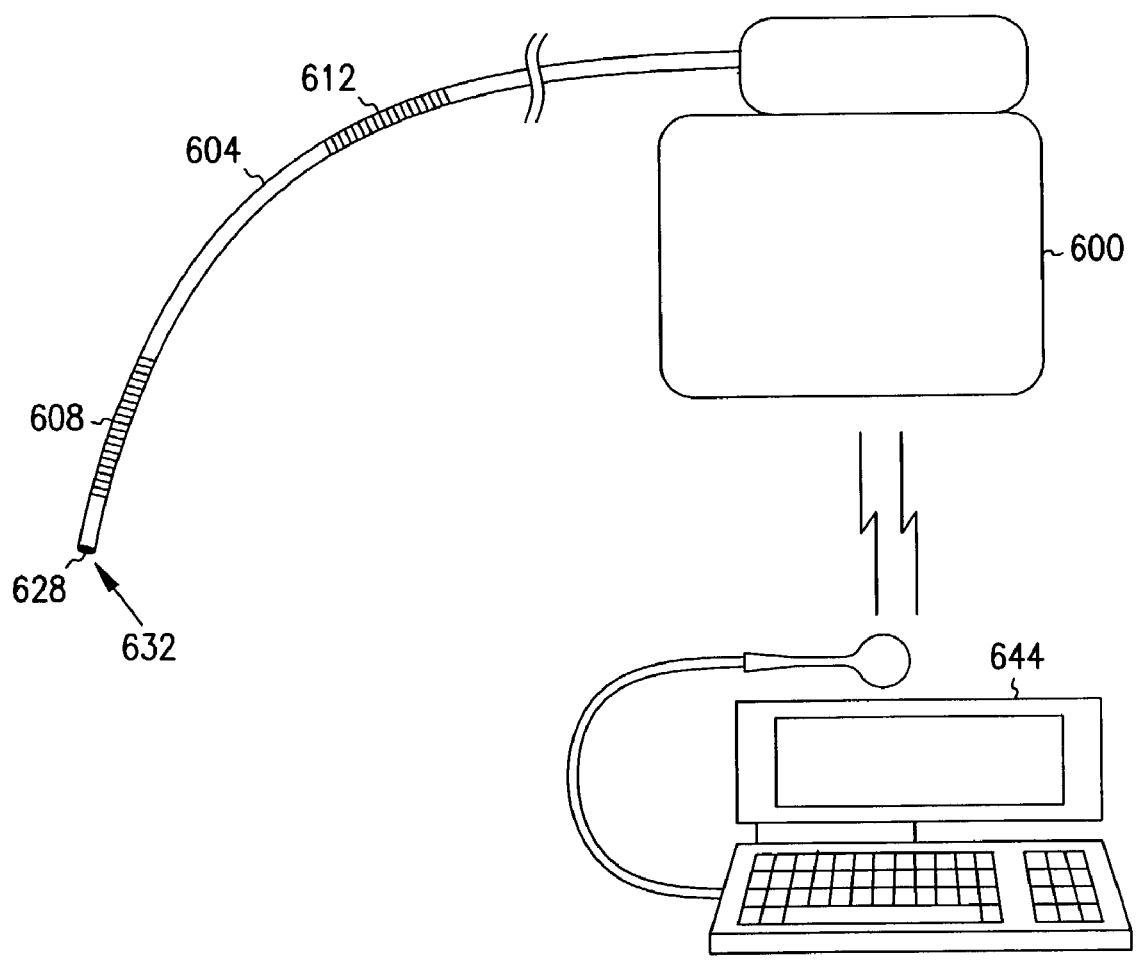
FIG. 6 is a schematic view of one embodiment of an implantable medical device according to one embodiment of the present subject matter.

Referring now to FIG. 6, there is shown one embodiment of a system according to the present subject matter. The system includes an implantable cardiac defibrillator 600 and at least one cardiac lead including at least three electrodes. In one embodiment, the at least one cardiac lead is a ventricular lead 604, where the ventricular lead 604 includes at least a first ventricular electrode 608 and a second ventricular electrode 612. FIG. 6 shows an embodiment in which the first ventricular electrode 608 is a defibrillation coil electrode positioned along a peripheral surface of the ventricular lead 604. The first ventricular electrode 608 is connected to the electronic circuitry within the implantable cardiac defibrillator 600 through a lead conductor housed and electrically insulated within the body of the ventricular lead 604. The second ventricular electrode 612 is also a defibrillation coil electrode which is positioned along the peripheral surface of the ventricular lead 604. The second ventricular electrode 612 is located at a position that is proximal to the first ventricular electrode 608 which allows for the ventricular lead 604 to be implanted within the vasculature with the first ventricular electrode 608 positioned in the right ventricle and the second ventricular electrode 612 positioned in either the right atrial chamber or a major vein leading to the right atrial chamber of the heart. In one embodiment, the first and second ventricular electrodes, 608 and 612, are used to sensed, or detect, a cardiac morphology signal from the heart. In one embodiment, the cardiac morphology signal sensed from the heart includes indicators of both atrial and ventricular depolarizations. In an additional embodiment, the electrically conductive portion of the implantable cardiac defibrillator 600 housing is used in conjunction with the first and second ventricular electrodes 608, 612 to allow for a morphology signal to be sensed between three electrodes.

In addition to the first and second ventricular electrodes 608, 612, the ventricular lead 604 is shown further including a pacing electrode 628 located at or adjacent a distal end 632 of the ventricular lead 604. This allows for both rate and morphology signals to be sensed from the ventricular region of the heart using the supplied electrodes, where, for example, the rate signal is sensed between the pacing electrode 628 and the first ventricular electrode 608 and the morphology signal is sensed between the first and second ventricular electrodes 608, 612.

Figure 7:
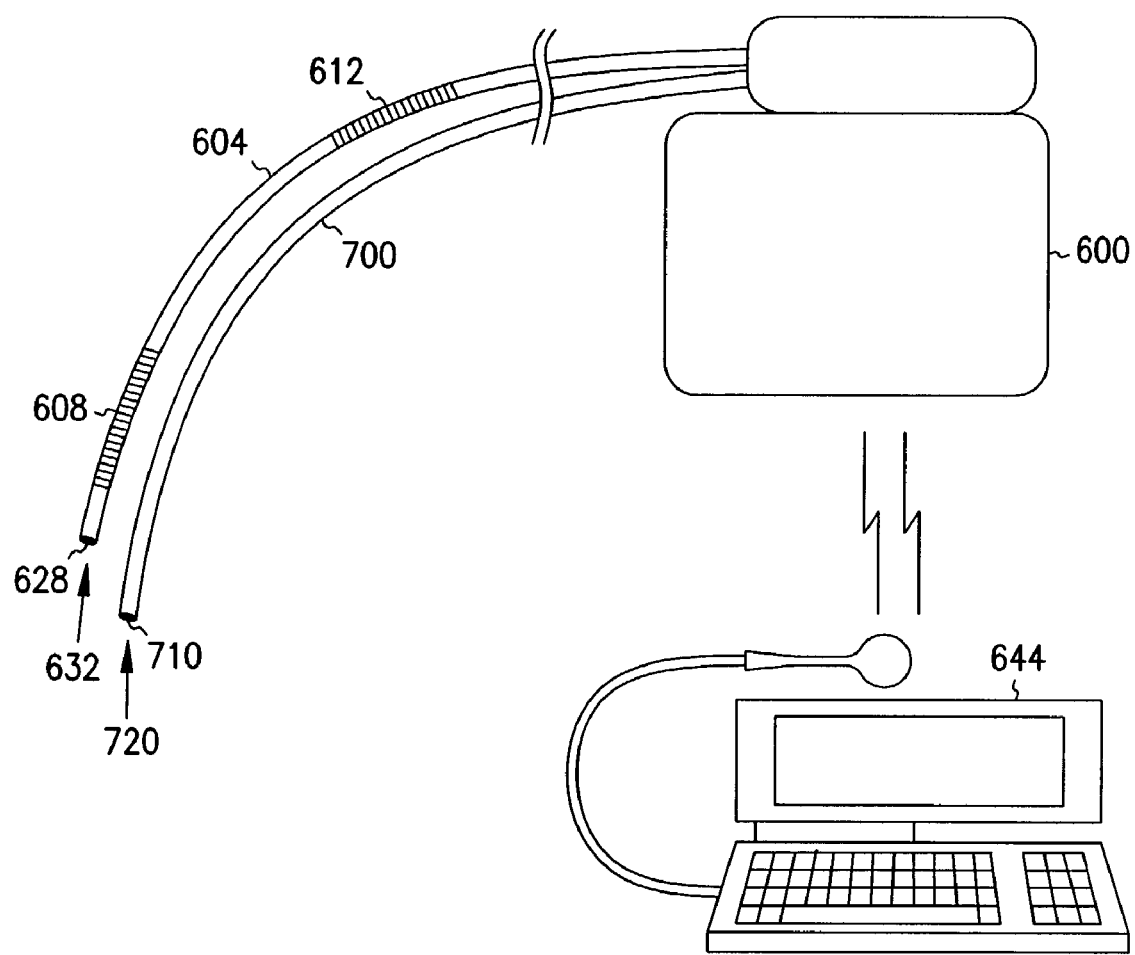
FIG. 7 is a schematic view of one embodiment of an implantable medical device according to one embodiment of the present subject matter.

Referring now to FIG. 7, there is shown an additional embodiment of the system according to the present subject matter. The system includes the implantable cardiac defibrillator 600, the ventricular lead 604 and an atrial lead 700. The atrial lead 700 includes a first atrial electrode 710, which in FIG. 7 is shown positioned at a distal end 720 of the atrial lead 700. The first atrial electrode 710 is connected to electronic circuitry within the implantable cardiac defibrillator 600 through a lead conductor housed and electrically insulated within the body of the atrial lead 700. The lead conductor allows for cardiac signals sensed using the first atrial electrode 710 to be supplied to the electronic circuitry and for pacing pulses generated though the use of the electronic circuitry to be delivered to the first atrial electrode 710. In the present embodiment, unipolar sensing and pacing is accomplished between the first atrial electrode 710 and an electrically conductive portion of the implantable cardiac defibrillator 600 housing.

In one embodiment, the atrial lead 700 and the ventricular lead 604 have elongated bodies made of one or more materials suitable for implantation in a human body, where such materials are known in the art. Additionally, the first and second ventricular electrodes 608, 612, the pacing electrode 628 and the first atrial electrode 710 are constructed of electrically conductive materials, such as platinum, platinum-iridium alloys, or other alloys as are known. The lead conductors are also constructed of electrically conductive materials such as MP35N, an alloy of nickel, chromium, cobalt, and molybdenum.

FIGS. 6 and 7 also shows a medical device programmer 644. The medical device programmer 644 and the implantable cardiac defibrillator 600 include communication circuitry which allows for cardiac data to be to and from the implantable cardiac defibrillator 600. In addition, command signals for controlling the operation of the implantable cardiac defibrillator 600 can also be sent between the medical device programmer 644 and the implantable cardiac defibrillator 600. In one embodiment, communication between the medical device programmer 644 and the implantable cardiac defibrillator 600 is established over a radio frequency telemetry channel as is known in the art.

Figure 8:
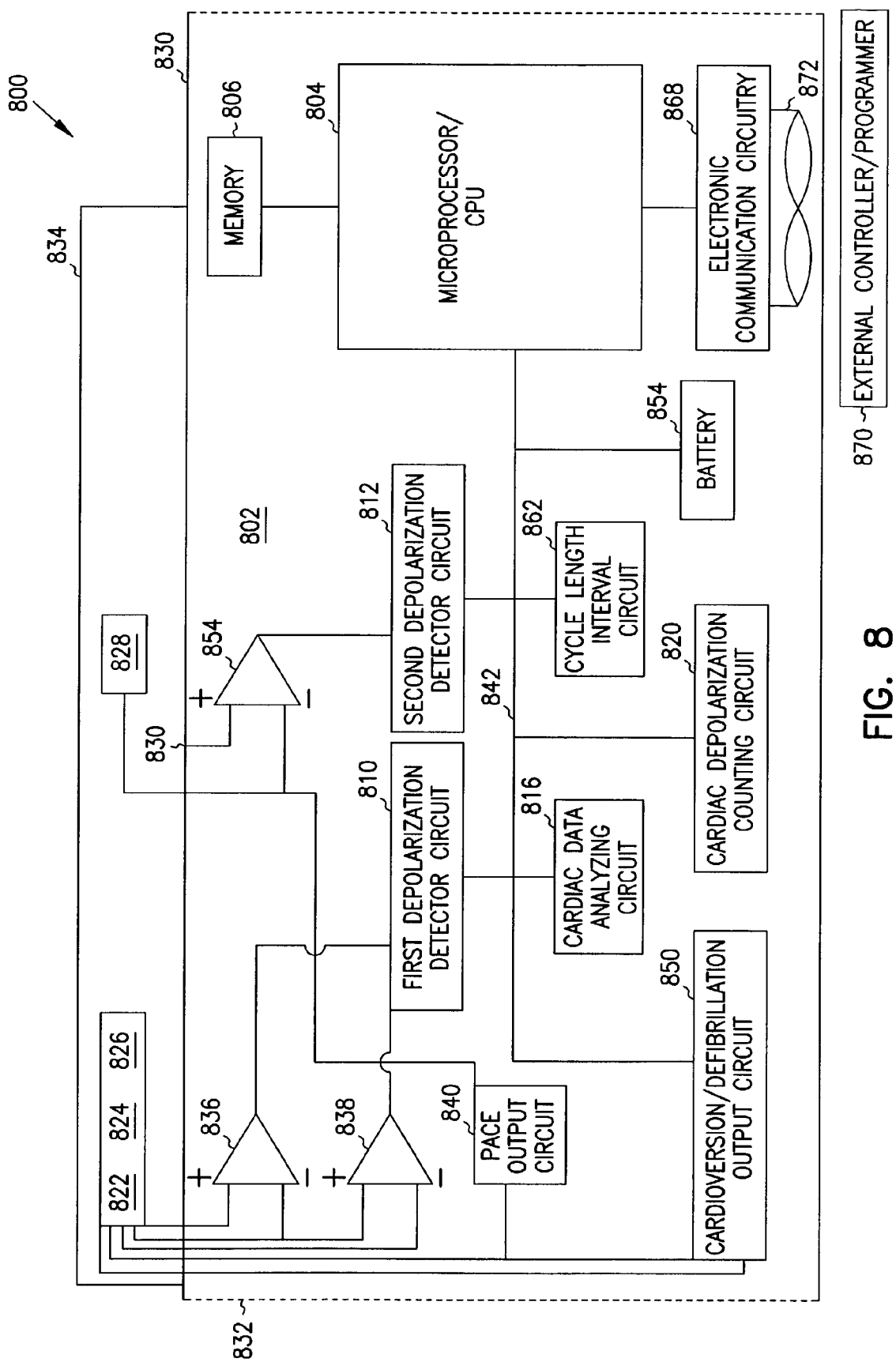
FIG. 8 is a block diagram of one embodiment of an implantable medical device according to the present subject matter.

Referring now to FIG. 8, there is shown a block diagram of an implantable cardiac defibrillator (ICD) 800 according to one embodiment of the present subject matter. The ICD 800 includes control circuitry 802 which receives one or more cardiac signals, generates electrical energy pulses under predetermined conditions, and can deliver electrical energy to electrodes positioned on the atrial and ventricular leads under the predetermined conditions.

In one embodiment, the control circuitry 802 is a programmable microprocessor-based system, with a microprocessor 804 and a memory circuit 806, which contains parameters for various pacing and sensing modes and stores data indicative of cardiac signals received by the control circuitry 802. The control circuitry 802 further includes a first depolarization detector circuit 810 to detect the occurrence of primary depolarizations in the first cardiac signal and a second depolarization detector circuit 812 to detect the occurrence of auxiliary depolarizations in the second cardiac signal.

A cardiac data analyzing circuit 816 is coupled to the first depolarization detector circuit 810 and the second depolarization detector circuit 812, where the cardiac data analyzing circuit 816 positions either the first time interval to surround each of one or more primary depolarizations of the primary depolarizations or the first time interval and the second time interval to surround the primary and auxiliary depolarizations as previously described. A cardiac depolarization counting circuit 820 is coupled to the cardiac data analyzing circuit 816, the first depolarization detector circuit 810 and the second depolarization detector circuit 812, where the cardiac depolarization counting circuit 820 counts auxiliary and/or primary depolarizations occurring in the first time interval and the first and second time intervals. The microprocessor 802, coupled to the cardiac depolarization counting circuit 820, classifies the primary depolarizations and the auxiliary depolarizations of the tachycardia episode as either associated or disassociated as previously described based on the depolarizations (auxiliary and/or primary) counted by the cardiac depolarization counting circuit 820.

In one embodiment, the control circuitry 802 includes terminals labeled with reference numbers 822, 824, 826, 828 and 830 for connection to at least three electrodes attached to the surface of the electrodes attached to the surface of the at least one cardiac lead. In the present embodiment, the terminals of the control circuitry are coupled to the ventricular lead and the atrial lead of FIG. 7. In the embodiment shown in FIG. 7, the first ventricular electrode 608 is coupled to terminal 822 through a first electrically insulated conductor provided within the ventricular lead 604. The second ventricular electrode 612 is coupled to terminal 824 through a second electrically insulated conductor provided within the ventricular lead 604. The pacing electrode 628 on the ventricular lead 604 is coupled to terminal 826 through a third electrically insulated conductor provided within the ventricular lead 604. Finally, the first atrial electrode 710 is coupled to terminals 828 by electrically insulated conductors provided within the atrial lead 700.

The control circuitry 802 is encased and hermetically sealed in a housing 832 suitable for implanting in a human body. In one embodiment, the housing 832 is made of titanium, however, other biocompatible housing materials as are known in the art may be used. A connector block 834 is additionally attached to the housing 832 to allow for the physical and the electrical attachment of the ventricular lead 604, the atrial lead 700 and the electrodes to the ICD 800 and the encased control circuitry 802.

In the present embodiment, there is shown sense amplifiers 836 and 838 coupled to the control circuitry 802, and electrically coupled to terminals 822, 824 and 826 to allow for a first cardiac signal to be sensed. In one embodiment, the first cardiac signal is sensed between the ventricular electrode 628 and first defibrillation electrode 608 and/or between the first ventricular electrode 608 and the second ventricular electrode 612. The output of the sense amplifiers 836 and 838 are connected to the first depolarization detector circuit 810 which is adapted to detect the occurrence of primary depolarizations in the first cardiac signal. In one embodiment, these components serve to sense near or far field cardiac signals and to amplify the signals indicating primary depolarizations, for example by sensing ventricular R-waves, QRS-complexes, or P-waves and apply signals indicative thereof to microprocessor 804. Among other things, the microprocessor 804 responds to the first depolarization detector 810 by providing pacing signals to a pace output circuit 840 via bus 842, as needed according to the programmed pacing mode.

In one embodiment, the pace output circuit 840 provides output pacing signals to the ventricular electrode 628 and first defibrillation electrode 608 via terminals 824 and 826. The first defibrillation electrode 608, the second defibrillation electrode 612 and the housing 820 are also coupled to a cardioversion/defibrillation output circuit 850 to provide pulses of either cardioversion or defibrillation electrical energy to the terminals 824 or 822 and the housing 832 under the control of the microprocessor 804. Power to the ICD 800 is supplied by an electrochemical battery 854 that is housed within the ICD 800.

The present embodiment further includes a sense amplifier 854, which is coupled to the control circuitry 802, and is electrically coupled to terminal 828 and 830 to allow for a second cardiac signal to be sensed. In one embodiment, the second cardiac signal is sense between the atrial electrode 710 and the housing 832. In an alternative embodiment, a second atrial electrode (not shown) can be added to the atrial lead 700 and be coupled to sense amplifier 854 to allow for bipolar sensing and pacing. The output of the sense amplifier 854 is connected to the second depolarization detector circuit 812 which is adapted to detect the occurrence of auxiliary depolarizations in the second cardiac signal. In one embodiment, these components serve to sense near or far field cardiac signals and to amplify the signals indicating primary depolarizations, for example by sensing ventricular R-waves, QRS-complexes, or P-waves and apply signals indicative thereof to microprocessor 804. Among other things, the microprocessor 804 responds to the second depolarization detector 812 by providing pacing signals to a pace output circuit 840 via bus 842, as needed according to the programmed pacing mode.

The control circuitry 802 further includes the cardiac data analyzing circuit 816, which is coupled to the first depolarization detector circuit 810, the microprocessor 804 and the memory circuit 806 via bus 842. In one embodiment, the cardiac data analyzing circuit 816 analyzes either primary and/or auxiliary depolarizations for the occurrence of a tachycardia episode. In one embodiment, when a tachycardia episode is identified, a cycle length interval circuit 862 coupled to the first and second depolarization detector circuits, 810 and 812, and the cardiac data analyzing circuit 816 is used to measures auxiliary cycle lengths between pairs of consecutively sensed auxiliary depolarizations and/or primary depolarizations over the measurement window interval as previously described. The cycle length interval circuit 862 calculates an average value ($XX_{avg}$) and a standard deviation value ($XX_{sd}$) of the auxiliary cycle lengths or of the auxiliary cycle lengths and the primary cycle lengths, as previously described. The cardiac data analyzing circuit 816 then calculates a first time interval or a first time interval and a second time interval as previously described, where the time interval is equal to ($X_{avg}$−$Y*XX_{sd}$) as previously described.

The cardiac data analyzing circuit 816 then positions the first time interval to surround one or more primary depolarizations and the auxiliary depolarizations in the first time interval. Alternatively, the cardiac data analyzing circuit 816 positions the first time interval and the second time interval to surround the primary and auxiliary depolarizations. In one embodiment, the cardiac data analyzing circuit positions the time interval (first and/or second) with the midpoint location of the time interval at the primary depolarization as previously described.

In an additional embodiment, the microprocessor compares K to threshold values $K_{low}$ and $K_{high}$ to determine when primary and auxiliary depolarizations are classified with a predetermined confidence level, as previously described. When the relationship of K to threshold values $K_{low}$ and $K_{high}$ shows that primary and auxiliary depolarizations are not classified with the predetermined confidence level, the microprocessor extends the measurement window interval, as previously described. Alternatively, the microprocessor stops the measurement window interval when the relationship of K to threshold values $K_{low}$ and $K_{high}$ shows that primary and auxiliary depolarizations are classified with the predetermined confidence level.

The cardiac depolarization counting circuit 820 receives the cardiac signals and counts the occurrences of cardiac depolarizations. In one embodiment, the cardiac depolarization counting circuit 820 counts the first number (K) of auxiliary depolarizations during the first-half of the first time intervals that precedes each of the one or more primary depolarizations. The cardiac depolarization counting circuit 820 can also count a total number (N) of auxiliary depolarizations during the first time interval that surround each of the one or more primary depolarizations. In an additional embodiment, the cardiac depolarization counting circuit 820 also counts a first number (L) and total number (M) of primary depolarizations that occur in the second time intervals positioned on the auxiliary depolarizations, as previously described.

The microprocessor 804 then receives the first and the total number of auxiliary depolarizations. In one embodiment, the microprocessor 804 classifies the auxiliary and primary depolarizations of the tachycardia episode as either associated or disassociated based on the values of the first (K) and total (N) numbers of auxiliary depolarizations. For example, the microprocessor 804 calculates the value for K/N, where in one embodiment, the microprocessor classifies the auxiliary depolarizations and the primary depolarizations of the tachycardia episode as either associated or disassociated based on the value of K/N. In one embodiment, the microprocessor 804 classifies the tachycardia episode as disassociated when the value of K/N is equal to approximately one-half (0.5).

Alternatively, the microprocessor 804 classifies the auxiliary depolarizations and the primary depolarizations of the tachycardia episode as either associated or disassociated based on whether K/N is statistically different from one-half (0.5) at the predetermined confidence level as previously described. For example, the microprocessor classifies the one or more primary depolarization and the auxiliary depolarizations as associated when K/N is statistically different from one-half (0.5) at a predetermined confidence level. Alternatively, the microprocessor classifies the one or more primary depolarizations and the auxiliary depolarizations as dissociated when K/N is not statistically different from one-half (0.5) at a predetermined confidence level. Also, the microprocessor can classifies the one or more primary depolarizations and the auxiliary depolarizations of the tachycardia episode as disassociated when K is less than or equal to $K_{low}$ or when K is greater than or equal to $K_{high}$, and classifies the one or more primary depolarizations and the auxiliary depolarizations of the tachycardia episode as associated when K is between $Kl_{ow}$ and $K_{high}$, as previously described.

In an additional embodiment, the first time intervals are positioned to surround each of the auxiliary depolarization instead of surrounding the one or more primary depolarization. Then, a second number (I) of primary depolarization is counted as the total number of primary depolarizations occurring in the second-half of the any of the first time intervals surrounding each of the auxiliary depolarizations. Also, a total number (J) of primary depolarization that occur anywhere in any of the first time intervals surrounding each of the auxiliary depolarizations is counted. Similar to the classifications based on K/N, the microprocessor 804 then classifies the auxiliary depolarizations and the primary depolarizations of the tachycardia episode as associated or dissociated based on I/J. In one embodiment, the microprocessor 804 classifies the auxiliary depolarizations and the primary depolarizations as dissociated when I/J is approximately equal to one-half (0.5). Alternatively, the microprocessor 804 classifies he auxiliary depolarizations and the primary depolarizations as associated when I/J is not approximately equal to one-half (0.5). In an additional embodiment, the microprocessor 804 classifies the auxiliary depolarizations and the primary depolarizations of the tachycardia episode as either associated or dissociated based on whether I/J is statistically different from one-half (0.5) at the predetermined confidence level as previously described.

In an additional embodiment, in addition to positioning the first time intervals to surround each of the auxiliary depolarizations in the second cardiac signal, the cardiac data analyzing circuit 816 also positions the second time intervals to surround each of the one or more primary depolarizations in the first cardiac signal. The cardiac depolarization counting circuit 820 then counts a first number (K) and total number (N) of auxiliary depolarizations occurring during the first time intervals surrounding each of the one or more primary depolarizations in the first cardiac signal. The cardiac depolarization counting circuit 820 also counts a first number (L) and total number (M) of primary depolarizations occurring during the second time intervals surrounding each of the one or more auxiliary depolarizations in the second cardiac signal. The microprocessor 804 then makes a first classification of the primary and auxiliary depolarizations based on K and N and makes a second classification of the primary and auxiliary depolarizations based on L and M, and then classifies the auxiliary depolarizations and the one or more primary depolarization as either associated or dissociated based on these first and second classifications as previously described.

As previously discussed, the auxiliary and primary depolarizations can be any combination of atrial and/or ventricular depolarizations sensed in one or more cardiac signals. In one embodiment, a first cardiac signal and a second cardiac signal are sensed, where the first cardiac signal includes indications of depolarizations in a first cardiac area and the second cardiac signal includes indications of depolarizations in a second cardiac area. In one embodiment, the first cardiac area includes at least one ventricular chamber, such as the right ventricular chamber, where the primary depolarizations would be ventricular depolarizations, and the second cardiac area includes at least one atrial chamber, such as the right atrial chamber, where the auxiliary depolarizations would be atrial depolarizations. In an alternative embodiment, the first cardiac area includes at least one atrial chamber and the second cardiac area includes at least one ventricular chamber.

The first and second cardiac areas can also be located in, or adjacent, the same cardiac region of the heart. For example, the first cardiac area can be in a first atrial chamber, where the primary depolarizations are first atrial chamber depolarizations, and the second cardiac area can be in a second atrial chamber, where the auxiliary depolarizations are second atrial chamber depolarizations. Alternatively, both the first cardiac area and the second cardiac area are from an atrial chamber (e.g., both from a right atrial chamber, or both from a left atrial chamber), where the primary depolarizations are atrial chamber first area depolarizations and the auxiliary depolarizations are atrial chamber second area depolarizations.

In a similar manner, the first cardiac area can be in, or adjacent, a first ventricular chamber, where the primary depolarizations are first ventricular chamber depolarizations, and the second cardiac area can be in a second ventricular chamber, where the auxiliary depolarizations are second ventricular chamber depolarizations. Alternatively, both the first cardiac area and the second cardiac area are from an ventricular chamber (e.g., both from a right ventricular chamber, or both from a left ventricular chamber area), where the primary depolarizations are ventricular chamber first area depolarizations and the auxiliary depolarizations are ventricular chamber second area depolarizations.

Electronic communication circuitry 868 is additionally coupled to the control circuitry 802 to allow the ICD 800 to communicate with an external controller 870. In one embodiment, the electronic communication circuitry 868 includes a data receiver and a data transmitter to send and receive and transmit signals and cardiac data to and from an external programmer 870. In one embodiment, the data receiver and the data transmitter include a wire loop antenna 872 to establish a radio frequency telemetric link, as is known in the art, to receive and transmit signals and data to and from the programmer unit 870.

This application is intended to cover any adaptations or variations of the present invention. It is manifestly intended that this invention be limited only by the claims and equivalents thereof.

What is claimed is:

1. A system, comprising:
control circuitry where the control circuitry receives a first cardiac signal and a second cardiac signal sensed during a cardiac episode, where the first cardiac signal includes indications of depolarizations in a first cardiac area and the second cardiac signal includes indications of depolarizations in a second cardiac area, the control circuitry including:
a first depolarization detector circuit to detect occurrence of primary depolarizations in the first cardiac signal;
a second depolarization detector circuit to detect occurrence of auxiliary depolarizations in the second cardiac signal;
a cardiac depolarization counting circuit coupled to the first depolarization detector circuit and the second depolarization detector circuit, where the cardiac depolarization counting circuit counts a first number (K) of auxiliary depolarizations occurring during a first portion of a first time interval surrounding each of one or more primary depolarizations of the primary depolarizations and counts a total number (N) of auxiliary depolarizations during the first time interval; and a microprocessor coupled to the cardiac depolarization counting circuit, where the microprocessor calculates K/N and determines whether the primary depolarizations and the auxiliary depolarizations in the cardiac episode are associated or disassociated based on K/N.

2. The system of claim 1, where the first time interval has an approximate midpoint location positioned at each of the one or more primary depolarizations, where the first portion of the first time interval is substantially a first-half of the first time interval, and where the microprocessor determines that the primary depolarizations and the auxiliary depolarizations in the cardiac episode are disassociated when K/N is equal to approximately one-half (0.5).

3. The system of claim 1, where the first time interval has an approximate midpoint location positioned at each of the one or more primary depolarizations, where the first portion of the first time interval is substantially a first-half of the first time interval, and where the microprocessor determines that the primary depolarizations and the auxiliary depolarizations in the cardiac episode are associated when K/N is not equal to approximately one-half (0.5).

4. The system of claim 1, where the first time interval has an approximate midpoint location positioned at each of the one or more primary depolarizations, where the first portion of the first time interval is substantially a first-half of the first time interval, and where the microprocessor determines that the primary depolarizations and the auxiliary depolarizations in the cardiac episode are associated when K/N is statistically different from one-half (0.5) at a predetermined confidence level and where the microprocessor determines that the primary depolarizations and the auxiliary depolarizations in the cardiac episode are disassociated when K/N is not statistically different from one-half (0.5) at the predetermined confidence level.

5. The system of claim 4, where the microprocessor determines that the primary depolarizations and the auxiliary depolarizations in the cardiac episode are disassociated when K is less than or equal to a first threshold value Klow or when K is greater than or equal to a second threshold value Khigh, and determines that the primary depolarizations and the auxiliary depolarizations in the cardiac episode are associated when K is between Klow and Khigh.

6. The system of claim 1, where the first time interval has an approximate midpoint location positioned at each of the one or more primary depolarizations, where the first portion of the first time interval is substantially a first-half of the first time interval, and where the cardiac depolarization counting circuit counts a second number (J) of auxiliary depolarizations during substantially a second-half of the first time interval, and the microprocessor determines that the primary depolarizations and the auxiliary depolarizations are associated when K and J are statistically different at a predetermined confidence level.

7. The system of claim 6, where the microprocessor determines that the primary depolarizations and the auxiliary depolarizations are disassociated when K and J are not statistically different at the predetermined confidence level.

8. A system, comprising:
control circuitry where the control circuitry receives a first cardiac signal and a second cardiac signal sensed during a cardiac episode, where the first cardiac signal includes indications of depolarizations in a first cardiac area and the second cardiac signal includes indications of depolarizations in a second cardiac area, the control circuitry including:

a first depolarization detector circuit to detect occurrence of primary depolarizations in the first cardiac signal;
a second depolarization detector circuit to detect occurrence of auxiliary depolarizations in the second cardiac signal;
a cycle length interval circuit coupled to the second depolarization detector circuit, where the cycle length interval circuit measures auxiliary cycle lengths between pairs of consecutively sensed auxiliary depolarizations in a measurement window interval;
a cardiac data analyzing circuit coupled to the cycle length interval circuit, where the cardiac data analyzing circuit calculates a first time interval based on an average value and an standard deviation value of the auxiliary cycle lengths and positions the first time interval to surround each of one or more primary depolarizations of the primary depolarizations;
a cardiac depolarization counting circuit coupled to the first depolarization detector circuit and the second depolarization detector circuit, where the cardiac depolarization counting circuit counts a number of auxiliary depolarizations occurring during the first time interval; and
a microprocessor coupled to the cardiac depolarization counting circuit, where the microprocessor determines whether the primary depolarizations and the auxiliary depolarizations in the cardiac episode are associated or disassociated based on the number of auxiliary depolarizations occurring during the first time interval.

9. The system of claim 8, wherein the cycle length interval circuit calculates an average value (XXavg) and an standard deviation value (XXsd) of the auxiliary cycle lengths, and where the cardiac data analyzing circuit calculates the first time interval equal to (XXavg−Y * XXsd), where Y is a predetermined constant.

10. The system of claim 9, where the measurement window interval has a predetermined duration.

11. The system of claim 9, where the measurement window interval has a duration sufficient to detect a predetermined number of primary depolarizations.

12. The system of claim 9, where the cardiac depolarization counting circuit counts a first number (K) of auxiliary depolarizations that occur during a first portion of the first time interval, and where the microprocessor compares K to threshold values Klow and Khigh to determine when the determination of whether the primary depolarizations and the auxiliary depolarizations in the cardiac episode are associated or disassociated can be made with a predetermined confidence level and extends the measurement window interval when the relationship of K to Klow and Khigh shows that the determination of whether the primary depolarizations and the auxiliary depolarizations in the cardiac episode are associated or disassociated cannot be made with the predetermined confidence level.

13. The system of claim 12, where the microprocessor repeats the measurement window interval when the relationship of K to Klow and Khigh shows that the determination of whether the primary depolarizations and the auxiliary depolarizations in the cardiac episode are associated or disassociated cannot be made with the predetermined confidence level.

14. The system of claim 12, where the microprocessor stops the measurement window interval when the relationship of K to Klow and Khigh shows that the determination of whether the primary depolarizations and the auxiliary depolarizations in the cardiac episode are associated or disassociated can be made with the predetermined confidence level.

15. A system, comprising:
control circuitry where the control circuitry receives a first cardiac signal and a second cardiac signal sensed during a cardiac episode, where the first cardiac signal includes indications of depolarizations in a first cardiac area and the second cardiac signal includes indications of depolarizations in a second cardiac area, the control circuitry including:
- a first depolarization detector circuit to detect occurrence of primary depolarizations in the first cardiac signal;
- a second depolarization detector circuit to detect occurrence of auxiliary depolarizations in the second cardiac signal;
- a cardiac data analyzing circuit coupled to the first depolarization detector circuit and the second depolarization detector circuit, where the cardiac data analyzing circuit positions a first time interval to surround each of one or more primary depolarizations of the primary depolarizations and a second time interval to surround each of one or more auxiliary depolarizations of the auxiliary depolarizations;
- a cardiac depolarization counting circuit coupled to the cardiac data analyzing circuit, where the cardiac depolarization counting circuit counts the number of auxiliary depolarizations occurring during the first time interval and the number of primary depolarizations occurring during the second time interval; and
- a microprocessor coupled to the cardiac depolarization counting circuit, where the microprocessor determines whether the primary depolarizations and the auxiliary depolarizations in the cardiac episode are associated or disassociated based on the number of primary depolarizations occurring during the second time interval and the number of auxiliary depolarizations occurring during the first time interval.

16. The system of claim 15, where the cardiac depolarization counting circuit counts a first number (K) of auxiliary depolarizations which occur during a first portion of the first time interval that at least substantially precedes each of the one or more primary depolarizations, counts a total number (N) of auxiliary depolarizations during the first time interval, counts a first number (L) of primary depolarizations which occur during a first portion of the second time interval that at least substantially precedes each of the one or more auxiliary depolarizations, and counts a total number (M) of primary depolarizations during the second time interval; and
where the microprocessor makes a first determination of whether the primary depolarizations and the auxiliary depolarizations in the cardiac episode are associated or disassociated based on K and N, makes a second determination of whether the primary depolarizations and the auxiliary depolarizations in the cardiac episode are associated or disassociated based on L and M, and makes an overall determination of whether the primary depolarizations and the auxiliary depolarizations in the cardiac episode are associated or disassociated based on outcomes of the first determination and the second determination.

17. The system of claim 16, where the first time interval and the second time interval each include an approximate midpoint location, and the cardiac data analyzing circuit positions the first time interval with the approximate midpoint location of the first time interval at each primary depolarization of the one or more primary depolarizations and positions the second time interval with the approximate midpoint location of the second timer interval at each auxiliary depolarization of the one or more auxiliary depolarizations, and where the first portion of the first time interval is substantially a first-half of the first time interval, and the first portion of the second time interval is substantially a first-half of the second time interval.

18. The system of claim 16, where the microprocessor determines that the primary depolarizations and the auxiliary depolarizations in the cardiac episode are associated when the outcomes of both the first determination and the second determination indicate that the primary depolarizations and the auxiliary depolarizations in the cardiac episode are associated.

19. The system of claim 16, where the microprocessor determines that the primary depolarizations and the auxiliary depolarizations in the cardiac episode are disassociated when the outcomes of both the first determination and the second determination indicate that the primary depolarizations and the auxiliary depolarizations in the cardiac episode are disassociated.

20. The system of claim 16, where the microprocessor determines that the primary depolarizations and the auxiliary depolarizations in the cardiac episode are associated when the outcome of either the first determination or the second determination indicates that the primary depolarizations and the auxiliary depolarizations in the cardiac episode are associated.

21. The system of claim 16, where the microprocessor determines that the primary depolarizations and the auxiliary depolarizations in the cardiac episode as disassociated when the outcome of either the first determination or the second determination indicates that the primary depolarizations and the auxiliary depolarizations in the cardiac episode are disassociated.

22. The system of claim 16, where the microprocessor calculates a statistical significance for each of the first determination and the second determination, and determines that the primary depolarizations and the auxiliary depolarizations in the cardiac episode are associated when the first determination and the second determination produce different outcomes and the outcome indicating that the primary depolarizations and the auxiliary depolarizations in the cardiac episode are associated has a higher statistical significance than the outcome indicating that the primary depolarizations and the auxiliary depolarizations in the cardiac episode are disassociated.

23. The system of claim 16, where the microprocessor calculates a statistical significance for each of the first determination and the second determination, and determines that the primary depolarizations and the auxiliary depolarizations in the cardiac episode are disassociated when the first determination and the second determination produce different outcomes and the outcome indicating that the primary depolarizations and the auxiliary depolarizations in the cardiac episode are disassociated has a higher statistical significance than the outcome indicating that the primary depolarizations and the auxiliary depolarizations in the cardiac episode are associated.

24. A method, comprising:
sensing at least one cardiac signal during a cardiac episode, where the at least one cardiac signal includes auxiliary depolarizations and primary depolarizations;
measuring auxiliary cycle lengths between pairs of consecutively sensed auxiliary depolarizations in a measurement window interval;
calculating an average value (XXavg) and a standard deviation value (XXsd) of the auxiliary cycle lengths;
calculating a first time interval, where the first time interval has a value equal to:

(XXavg−Y * XXsd), where Y is a predetermined constant; positioning the first time interval to surround each of one or more primary depolarizations of the primary depolarizations;
counting auxiliary depolarizations over the first time interval; and
determining whether the primary depolarizations and the auxiliary depolarizations in the cardiac episode are disassociated or associated based on a number of the auxiliary depolarizations counted over the first time interval.

25. The method of claim 24, including programming a predetermined duration for the measurement window interval.

26. The method of claim 24, including programming a predetermined number of primary depolarizations defining the measurement window interval.

27. The method of claim 24, where the first time interval includes a first portion, and counting auxiliary depolarizations during the first time interval includes counting a first number (K) of auxiliary depolarizations during the first portion of the first time interval.

28. The method of claim 27, where the first portion of the first time interval is substantially a first-half of the first time interval.

29. The method of claim 28, further including:
comparing K to threshold values Klow and Khigh to classify the primary and auxiliary depolarizations at a predetermined confidence level; and
extending the measurement window interval when the relationship of K to threshold values Klow and Khigh shows that primary and auxiliary depolarizations are not classified with the predetermined confidence level.

30. The method of claim 28, where determining whether the primary depolarizations and the auxiliary depolarizations in the cardiac episode are disassociated or associated includes determining that the primary depolarizations and the auxiliary depolarizations in the cardiac episode are associated when K is less than or equal to a first threshold value Klow or greater than or equal to a second threshold value Khigh.

31. The method of claim 28, where determining whether the primary depolarizations and the auxiliary depolarizations in the cardiac episode are disassociated or associated includes determining that the primary depolarizations and the auxiliary depolarizations in the cardiac episode are disassociated when K is between a first threshold value Klow and a second threshold value Khigh.

32. A method, comprising:
sensing at least one cardiac signal during a cardiac episode, where the at least one cardiac signal includes auxiliary depolarizations and primary depolarizations;
counting a total number (N) of auxiliary depolarizations over a first time interval surrounding each of one or more primary depolarizations of the primary depolarizations;
counting a first number (K) of auxiliary depolarizations over a first portion of the first time interval;
calculating K/N; and
determining whether the primary depolarizations and the auxiliary depolarizations in the cardiac episode are disassociated or associated based on K/N.

33. The method of claim 32, where determining whether the primary depolarizations and the auxiliary depolarizations in the cardiac episode are disassociated or associated includes determining that the primary depolarizations and the auxiliary depolarizations in the cardiac episode are disassociated when K/N is equal to approximately one-half (0.5).

34. The method of claim 32, where determining whether the primary depolarizations and the auxiliary depolarizations in the cardiac episode are disassociated or associated includes determining that the primary depolarizations and the auxiliary depolarizations in the cardiac episode are associated when K/N is not equal to approximately one-half (0.5).

35. A method, comprising:
sensing at least one cardiac signal during a cardiac episode, where the at least one cardiac signal includes auxiliary depolarizations and primary depolarizations;
positioning a first time interval having an approximate midpoint location to surround each of one or more primary depolarizations of the primary depolarizations such that the approximate midpoint location is positioned at each of the one or more primary depolarizations;
counting auxiliary depolarizations over the first time interval; and
determining whether the primary depolarizations and the auxiliary depolarizations in the cardiac episode are disassociated or associated based on a number of the auxiliary depolarizations counted over the first time interval.

36. The method of claim 35, where the first time interval includes a first portion preceding the approximate midpoint location and a second portion which is subsequent to the approximate midpoint location, where counting the auxiliary depolarizations includes counting a first number of auxiliary depolarizations in the first portion of the first time interval, and a second number of auxiliary depolarizations in the second portion of the first time interval, and determining whether the first number and the second number are statistically different at a predetermined confidence level.

37. The method of claim 36, where determining whether the primary depolarizations and the auxiliary depolarizations in the cardiac episode are disassociated or associated includes determining that the primary depolarizations and the auxiliary depolarizations are associated if the first number of auxiliary depolarizations and the second number of auxiliary depolarizations are statistically different at the predetermined confidence level.

38. The method of claim 36, where determining whether the primary depolarizations and the auxiliary depolarizations in the cardiac episode are disassociated or associated includes determining that the primary depolarizations and the auxiliary depolarizations are disassociated if the first number of auxiliary depolarizations and the second number of auxiliary depolarizations are not statistically different at the predetermined confidence level.

39. The method of claim 36, including calculating the first portion and the second portion of the first time interval with an equation:

(XXavg−Y * XXsd)/2, where Y is a predetermined constant.

40. The method of claim 36, including:
counting a first number of primary depolarizations during a first portion of a second time interval surrounding the one or more auxiliary depolarizations;
counting a second number of primary depolarizations during a second portion of the second time interval; and
determining whether the primary depolarizations and the auxiliary depolarizations in the cardiac episode are disassociated or associated based on the first number of primary depolarizations, the second number of primary depolarizations, the first number of auxiliary depolarizations and the second number of auxiliary depolarizations.

41. A method, comprising:
sensing at least one cardiac signal during a cardiac episode, where the at least one cardiac signal includes auxiliary depolarizations and primary depolarizations;
counting the auxiliary depolarizations over a first time interval surrounding each of one or more primary depolarizations of the primary depolarizations;
counting the primary depolarizations over a second time interval surrounding each of one or more auxiliary depolarizations of the auxiliary depolarizations; and
determining whether the primary depolarizations and the auxiliary depolarizations in the cardiac episode are disassociated or associated based on a number of the auxiliary depolarizations counted over the first time interval and a number of the primary depolarizations counted over the second time interval.

42. The method of claim 41, comprising:
counting a first number (K) of auxiliary depolarizations over a first portion of the first time interval that precedes the each of one or more primary depolarizations;
counting a total number (N) of auxiliary depolarizations over the first time interval;
counting a first number (L) of primary depolarizations over a first portion of the second time interval that precedes each of the one or more auxiliary depolarizations;
counting a total number (M) of primary depolarizations over the second time interval;
making a first determination of whether the primary depolarizations and the auxiliary depolarizations in the cardiac episode are disassociated or associated based on K and N;
making a second determination of whether the primary depolarizations and the auxiliary depolarizations in the cardiac episode are disassociated or associated based on L and M; and
determining whether the primary depolarizations and the auxiliary depolarizations in the cardiac episode are disassociated or associated based on outcomes of the first determination and the second determination.

43. The system of claim 42, where the first portion of the first time interval is substantially a first-half of the first time interval, and the first portion of the second time interval is substantially a first-half of the second time interval.

44. The method of claim 42, where determining whether the primary depolarizations and the auxiliary depolarizations in the cardiac episode are disassociated or associated includes determining that the primary depolarizations and the auxiliary depolarizations in the cardiac episode are associated when the outcomes of both the first determination and the second determination indicate that the primary depolarizations and the auxiliary depolarizations in the cardiac episode are associated.

45. The method of claim 42, where determining whether the primary depolarizations and the auxiliary depolarizations in the cardiac episode are disassociated or associated includes determining that the primary depolarizations and the auxiliary depolarizations in the cardiac episode are disassociated when the outcomes of both the first determination and the second determination indicate that the primary depolarizations and the auxiliary depolarizations in the cardiac episode are disassociated.

46. The method of claim 42, where determining whether the primary depolarizations and the auxiliary depolarizations in the cardiac episode are disassociated or associated includes determining that the primary depolarizations and the auxiliary depolarizations in the cardiac episode are associated when the outcome of either the first determination or the second determination indicates that the primary depolarizations and the auxiliary depolarizations in the cardiac episode are associated.

47. The method of claim 42, where determining whether the primary depolarizations and the auxiliary depolarizations in the cardiac episode are disassociated or associated includes determining that the primary depolarizations and the auxiliary depolarizations in the cardiac episode are disassociated when the outcome of either the first determination or the second determination indicates that the primary depolarizations and the auxiliary depolarizations in the cardiac episode are disassociated.

48. The method of claim 42, including calculating a statistical significance for each of the results of the first determination and the second determination, and determining that the primary depolarizations and the auxiliary depolarizations in the cardiac episode are associated when the first determination and the second determination produce different outcomes and the outcome indicating that the primary depolarizations and the auxiliary depolarizations in the cardiac episode are associated has a higher statistical significance than the outcome indicating that the primary depolarizations and the auxiliary depolarizations in the cardiac episode are disassociated.

49. The method of claim 42, including calculating a statistical significance for each of the results of the first determination and the second determination, and determining that the primary depolarizations and the auxiliary depolarizations in the cardiac episode are disassociated when the first determination and the second determination produce different outcomes and the outcome indicating that the primary depolarizations and the auxiliary depolarizations in the cardiac episode are disassociated has a higher statistical significance than the outcome indicating that the primary depolarizations and the auxiliary depolarizations in the cardiac episode are associated.

* * * * *

UNITED STATES PATENT AND TRADEMARK OFFICE
CERTIFICATE OF CORRECTION

PATENT NO. : 7,151,958 B2
APPLICATION NO. : 10/211222
DATED : December 19, 2006
INVENTOR(S) : Hsu et al.

It is certified that error appears in the above-identified patent and that said Letters Patent is hereby corrected as shown below:

In column 21, line 39, in Claim 5, delete "Klow" and insert -- $K_{low}$ --, therefor.

In column 21, line 41, in Claim 5, delete "Khigh," and insert -- $K_{high,}$ --, therefor.

In column 21, line 43, in Claim 5, delete "Klow and Khigh." and insert -- $K_{low}$ and $K_{high}$. --, therefor.

In column 22, line 34, in Claim 9, delete "(XXavg)" and insert -- $(XX_{avg})$ --, therefor.

In column 22, line 35, in Claim 9, delete "(XXsd)" and insert -- $(XX_{sd})$ --, therefor.

In column 22, line 39, in Claim 9, delete "(XXavg–Y * XXsd)" and insert -- $(XX_{avg}-Y * XX_{sd})$, --, therefor.

In column 22, line 51, in Claim 12, delete "Klow and Khigh" and insert -- $K_{low}$ and $K_{high}$ --, therefor.

In column 22, line 56, in Claim 12, delete "Klow and Khigh" and insert -- $K_{low}$ and $K_{high}$ --, therefor.

In column 22, line 63, in Claim 13, delete "Klow and Khigh" and insert -- $K_{low}$ and $K_{high}$ --, therefor.

In column 23, line 3, in Claim 14, delete "Klow and Khigh" and insert -- $K_{low}$ and $K_{high}$ --, therefor.

In column 24, line 8, in Claim 17, delete "timer" and insert -- time --, therefor.

In column 25, line 8, in Claim 24, delete "(XXavg)" and insert -- $(XX_{avg})$ --, therefor.

In column 25, line 9, in Claim 24, delete "(XXsd)" and insert -- $(XX_{sd})$ --, therefor.

In column 25, line 13, in Claim 24, delete "(XXavg–Y * XXsd)," and insert -- $(XX_{avg}-Y * XX_{sd})$, --, therefor.

In column 25, line 41, in Claim 29, delete "Klow and Khigh" and insert -- $K_{low}$ and $K_{high}$ --, therefor.

UNITED STATES PATENT AND TRADEMARK OFFICE
CERTIFICATE OF CORRECTION

PATENT NO. : 7,151,958 B2
APPLICATION NO. : 10/211222
DATED : December 19, 2006
INVENTOR(S) : Hsu et al.

It is certified that error appears in the above-identified patent and that said Letters Patent is hereby corrected as shown below:

In column 25, line 45, in Claim 29, delete "Klow and Khigh" and insert -- $K_{low}$ and $K_{high}$ --, therefor.

In column 25, line 54, in Claim 30, delete "Klow" and insert -- $K_{low}$ --, therefor.

In column 25, line 55, in Claim 30, delete "Khigh." and insert -- $K_{high}$. --, therefor.

In column 25, line 62, in Claim 31, delete "Klow" and insert -- $K_{low}$ --, therefor.

In column 25, line 62, in Claim 31, delete "Khigh." and insert -- $K_{high}$. --, therefor.

In column 27, line 4, in Claim 39, delete "(XXavg–Y * XXsd)" and insert -- $(XX_{avg} - Y * XX_{sd})$, --, therefor.

Signed and Sealed this

Thirteenth Day of March, 2007

JON W. DUDAS
*Director of the United States Patent and Trademark Office*